(12) United States Patent
Cochran et al.

(10) Patent No.: US 10,968,173 B2
(45) Date of Patent: Apr. 6, 2021

(54) THIOCARBONYLTHIO COMPOUNDS AS CHAIN TRANSFER AGENTS SUITABLE FOR RAFT POLYMERIZATION

(71) Applicant: IOWA STATE UNIVERSITY RESEARCH FOUNDATION, INC., Ames, IA (US)

(72) Inventors: Eric W. Cochran, Ames, IA (US); Nacu Hernandez, Ames, IA (US); Michael Forrester, Ames, IA (US); Austin Hohmann, Dubuque, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 113 days.

(21) Appl. No.: 16/315,432

(22) PCT Filed: Jul. 7, 2017

(86) PCT No.: PCT/US2017/041144
§ 371 (c)(1),
(2) Date: Jan. 4, 2019

(87) PCT Pub. No.: WO2018/009830
PCT Pub. Date: Jan. 11, 2018

(65) Prior Publication Data
US 2019/0241512 A1 Aug. 8, 2019

Related U.S. Application Data

(60) Provisional application No. 62/359,474, filed on Jul. 7, 2016.

(51) Int. Cl.
C07C 327/36 (2006.01)
C07D 207/327 (2006.01)
(Continued)

(52) U.S. Cl.
CPC .......... *C07C 327/36* (2013.01); *C07C 329/00* (2013.01); *C07C 329/16* (2013.01);
(Continued)

(58) Field of Classification Search
CPC ........................... C07C 327/36; C07C 329/00
See application file for complete search history.

(56) References Cited

U.S. PATENT DOCUMENTS

| 6,512,081 | B1 | 1/2003 | Rizzardo et al. | |
| 2014/0343192 | A1* | 11/2014 | Cochran | C08F 242/00 |
| | | | | 523/436 |
| 2015/0073109 | A1* | 3/2015 | Benicewicz | C07C 329/00 |
| | | | | 526/193 |

FOREIGN PATENT DOCUMENTS

| EP | 0910587 B1 | 12/2001 |
| JP | 2006-045387 | * 2/2006 |

(Continued)

OTHER PUBLICATIONS

Translation of JP 2006-045387 (2006) (Year: 2006).*
(Continued)

*Primary Examiner* — Robert C Boyle
(74) *Attorney, Agent, or Firm* — Troutman Pepper Hamilton Sanders LLP (Rochester)

(57) ABSTRACT

The present invention relates to a compound having the structure of formula (I), wherein $R^1$, $R^2$, $R^3$, $R^4$, $R^5$, $R^6$, and $R^7$ are as described herein. The present invention also relates to a process for the preparation of a compound of formula (I) and to a process for the synthesis of a polymer using the compound of formula (I) through controlled free radical polymerization.

(Continued)

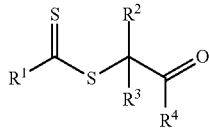

(I)

78 Claims, 22 Drawing Sheets

(51) Int. Cl.
C07C 329/00 (2006.01)
C07C 329/16 (2006.01)
C08F 293/00 (2006.01)

(52) U.S. Cl.
CPC ...... *C07D 207/327* (2013.01); *C08F 293/005* (2013.01); *C08F 2438/02* (2013.01); *C08F 2438/03* (2013.01)

(56) References Cited

FOREIGN PATENT DOCUMENTS

| JP | 2006045387 A | 2/2006 |
|----|--------------|--------|
| WO | 2008/089518 A1 | 7/2008 |

OTHER PUBLICATIONS

Haley, J. Org. Chem. 1980, 45, p. 175-177 (Year: 1980).*
Haley, Journal of Organic Chemistry (1980), 45(1), 175-7 (Year: 1980).*
Moore, Journal of the Chemical Society, Perkin Transactions 1: Organic and Bio-Organic Chemistry (1972-1999) (1991), (1), 157-68 (Year: 1991).*
Bryce, Journal of the Chemical Society, Perkin Transactions 1: Organic and Bio-Organic Chemistry (1972-1999) (1994), (18), 2571-8 (Year: 1994).*
International Search Report and Written Opinion for corresponding Application No. PCT/US2017/041144 (dated Nov. 8, 2017).
Bryce et al., "Substituted 1,4,2-Dithiazines: Synthesis by Ring Expansion of 1,3-Dithiolium Cations, Solution Redox Properties and X-Ray Crystal Structures of a Monocyclic and Bicyclic Derivative," J. Chem Soc. Perkin Trans. 18:2295-2302 (1992).
Moad et al., "Living Radical Polymerization by the RAFT Process—A First Update," Aust. J. Chem. 59:669-92 (2006).
Moad et al., "Living Radical Polymerization by the RAFT Process—A Second Update," Aust. J. Chem. 62:1402-72 (2009).
Moad et al., "Living Radical Polymerization by the RAFT Process—A Third Update," Aust. J. Chem. 65:985-1076 (2012).
International Preliminary Report on Patentability for corresponding Application No. PCT/US2017/041144 (dated Jan. 17, 2019).

* cited by examiner

THIOCARBONYLTHIO COMPOUNDS AS CHAIN TRANSFER AGENTS SUITABLE FOR RAFT POLYMERIZATION

This application is a national stage application under 35 U.S.C. § 371 of International Application No. PCT/US2017/041144, filed Jul. 7, 2017, which claims the benefit of U.S. Provisional Patent Application Ser. No. 62/359,474, filed Jul. 7, 2016, which are hereby incorporated by reference in their entirety.

FIELD OF THE INVENTION

The present invention relates to a chain transfer agents suitable for RAFT polymerization.

BACKGROUND OF THE INVENTION

Reversible addition fragmentation chain transfer, or RAFT, is a type of controlled free radical polymerization that has seen remarkable growth in research (Moad et al., "Living Radical Polymerization by the RAFT Process," *Aust. J. Chem.* 58:379-410 (2005)), due to its compatibility with various different monomer types (Moad et al., "Living Radical Polymerization by the RAFT Process," *Aust. J. Chem.* 58:379-410 (2005)), its ability to be carried out in various different solvents (Moad et al., "Living Radical Polymerization by the RAFT Process," *Aust. J. Chem.* 58:379-410 (2005))—including water (Derry et al., "Polymerization-Induced Self-Assembly of Block Copolymer Nanoparticles via RAFT Non-Aqueous Dispersion Polymerization," *Progress in Polymer Science* 52:1-18 (2016)), its ability to make block copolymers (Moad et al., "Living Radical Polymerization by the RAFT Process—A Third Update," *Aust. J. Chem.* 65:985-1076 (2012)), and the relatively low temperatures and pressures used (Hill et al., "Expanding the Scope of RAFT Polymerization: Recent Advances and New Horizons," *Macromolecules* 48(16): 5459-5469 (2015)). Despite the interest in the academic world, RAFT has yet to take off in industry-most probably and significantly due to the high cost of the production or purchase of chain transfer agents, or CTAs.

CTAs are chemicals that function to control the polymerization of monomers to give a specific molecular weight as well as a low polydispersity index (PDI), due to the CTA limiting the concentration of free radicals available (Hill et al., "Expanding the Scope of RAFT Polymerization: Recent Advances and New Horizons," *Macromolecules* 48(16): 5459-5469 (2015)). There are multiple types of CTA's (Moad et al., "Advances in Switchable RAFT Polymerization," *Macromolecular Symposia* 350(1):34-42 (2015); Moad et al., "Living Radical Polymerization by the RAFT Process—A First Update," *Aust. J. Chem.* 59:669-692. (2006); Moad et al., "Living Radical Polymerization by the RAFT Process—A Second Update," *Aust. J. Chem.* 62:1402-1472 (2009); Moad et al., "Living Radical Polymerization by the RAFT Process—A Third Update," *Aust. J. Chem.* 65:985-1076 (2012); Faber et al., "Highly Ordered Structure Formation in RAFT-Synthesized PtBOS-b-P4VP Diblock Copolymers," *Macromol. Rapid Commun.* 37(11): 911-919 (2016); Foster et al., "Norbornene-Containing Dithiocarbamates for Use in Reversible Addition-Fragmentation Chain Transfer (RAFT) Polymerization and Ring-Opening Metathesis Polymerization (ROMP)," *Polymer* 79:205-211 (2015)). In general, they follow the chemical structure shown in FIG. 1. The most commonly published Z group is phenyl dithioesters where a phenyl ring is the Z group. One of the challenging things about these types of CTAs is that they are typically based on Grignard reagents which have a number of side reactions and impurities that are present, making purification time consuming and expensive (Xu et al., "Aminolysis of Polymers with Thiocarbonylthio Termini Prepared by RAFT Polymerization: The Difference Between Polystyrene and Polymethacrylates," *Macromolecules* 39(25):8616-8624 (2006)). For example, the synthesis of cumyl benzodithioate, a very commonly used CTA for acrylates, styrenics, and methacrylates, typically gets less than 50% yield and requires use of column chromatography to purify the product to 95%+ purity (Jia et al., "Preparation and Characterization of Novel Organic/Inorganic Hybrid Nanoparticles Containing an Organotin Core and a Polystyrene Shell," *J. Appl. Polym. Sci.* 126(1):56-65 (2012)). This makes it a very difficult molecule to scale to industrial quantities. In addition to this purity issue, RAFT suffers from being rather slow in the polymerization of styrenics (Jia et al., "Preparation and Characterization of Novel Organic/Inorganic Hybrid Nanoparticles Containing an Organotin Core and a Polystyrene Shell," *J. Appl. Polym. Sci.* 126(1):56-65 (2012)).

The present invention is directed to overcoming these and other deficiencies in the art.

SUMMARY OF THE INVENTION

One aspect of the present invention relates to a compound having the structure of formula (I):

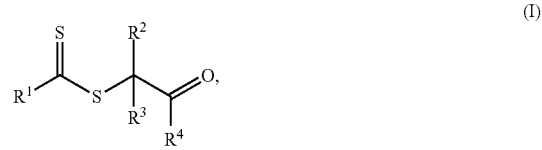

(I)

wherein
$R^1$ is aryl or $-SC_{1-20}$ alkyl, wherein the aryl and $-SC_{1-20}$ alkyl can be optionally substituted with 1-5 substituents independently selected in each occurrence thereof from the group consisting of H, $C_{1-6}$ alkyl, halogen, $-OR^5$, $-SR^5$, and $-NR^6R^7$,
$R^2$ is $C_{1-6}$ alkyl,
$R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl,
with the proviso that when $R^4$ is methyl then $R^1$ is not aryl or —S-t-Bu.

Another aspect of the present invention relates to a process for the preparation of a compound of formula (I):

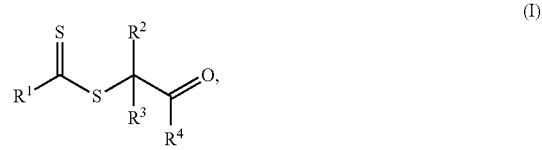

(I)

wherein
$R^1$ is aryl or $-SC_{1-20}$ alkyl, wherein the aryl and $-SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl, with the proviso that when $R^4$ is methyl then $R^1$ is not aryl or —S-t-Bu. The process comprises providing a first intermediate compound of formula (II):

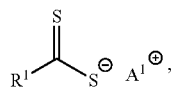
(II)

wherein $A^{1\oplus}$ is a suitable cation; and forming the compound of formula (I) from the first intermediate compound of formula (II).

Another aspect of the present invention relates to a process for the synthesis of a polymer. This process comprises
providing a monomer composition;
providing a chain transfer agent of formula (I):

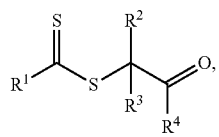
(I)

wherein
$R^1$ is aryl or —$SC_{1-20}$ alkyl, wherein aryl and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl; and polymerizing the monomer composition through controlled free radical polymerization with the chain transfer agent to form the polymer.

Another aspect of the present invention relates to a compound having the structure of formula (I):

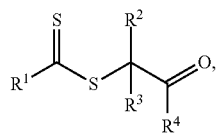
(I)

wherein
$R^1$ is aryl, heteroaryl, heterocyclyl, or —$SC_{1-20}$ alkyl, wherein the aryl, heteroaryl, heterocyclyl, and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H, $C_{1-6}$ alkyl, or —C(O)—$(CH_2)_n$—COOH,
$R^6$ is H or $C_{1-6}$ alkyl,
$R^7$ is H or $C_{1-6}$ alkyl, and
n is 1, 2, 3, 4, 5, or 6, with the proviso that when $R^4$ is methyl then $R^1$ is not aryl or —S-t-Bu.

Yet another aspect of the present invention relates to a process for the preparation of a compound of formula (I):

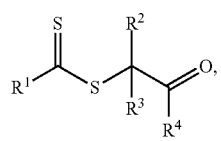
(I)

wherein
$R^1$ is aryl, heteroaryl, heterocyclyl, or —$SC_{1-20}$ alkyl, wherein the aryl, heteroaryl, heterocyclyl, and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H, $C_{1-6}$ alkyl, or —C(O)—$(CH_2)_n$—COOH,
$R^6$ is H or $C_{1-6}$ alkyl,
$R^7$ is H or $C_{1-6}$ alkyl, and
n is 1, 2, 3, 4, 5, or 6, with the proviso that when $R^4$ is methyl then $R^1$ is not aryl or —S-t-Bu. The process comprises providing a first intermediate compound of formula (II):

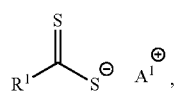
(II)

wherein $A^{1\oplus}$ is a suitable cation; and forming the compound of formula (I) from the first intermediate compound of formula (II).

Another aspect of the present invention relates to a process for the synthesis of a polymer. This process comprises
providing a monomer composition;
providing a chain transfer agent of formula (I):

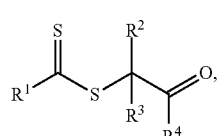
(I)

wherein

R¹ is aryl, heteroaryl, heterocyclyl, or —SC$_{1-20}$ alkyl, wherein the aryl, heteroaryl, heterocyclyl, and —SC$_{1-20}$ alkyl can be optionally substituted with 1-5 substituents independently selected in each occurrence thereof from the group consisting of H, C$_{1-6}$ alkyl, halogen, —OR⁵, —SR⁵, and —NR⁶R⁷, R² is C$_{1-6}$ alkyl,
R³ is H or C$_{1-6}$ alkyl,
R⁴ is H or C$_{1-6}$ alkyl,
R⁵ is H, C$_{1-6}$ alkyl, or —C(O)—(CH$_2$) n-COOH,
R⁶ is H or C$_{1-6}$ alkyl,
R⁷ is H or C$_{1-6}$ alkyl, and
n is 1, 2, 3, 4, 5, or 6, and polymerizing the monomer composition through controlled free radical polymerization with the chain transfer agent to form the polymer.

The present application addresses two of the challenges of the RAFT process. First, an R group is presented that works quite well for both dithioester and trithiocarbonates (FIGS. 2A-B), works well for acrylates and styrenics, and has a very simple, clean synthesis with very minimal purification steps even for Grignard based dithioates. Secondly, the slow polymerization rate of styrene was improved using RAFT. This is addressed by modifying the standard conditions used by the RAFT process with use of a trithioate.

BRIEF DESCRIPTION OF THE DRAWINGS

FIG. 2A shows the structure for 3-oxobutan-2-yl benzodithioate.

FIG. 2B shows the structure for ethyl (3-oxobutan-2-yl) carbonotrithioate (OXCART).

DETAILED DESCRIPTION OF THE INVENTION

Figure 1:
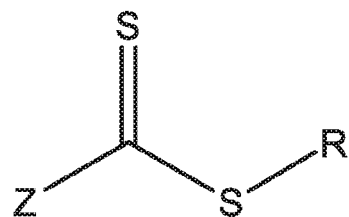
FIG. 1 shows generic CTA structure.
Figure 2A:
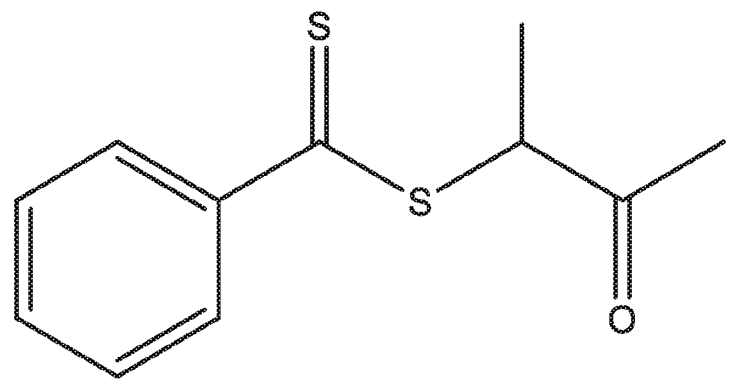
FIGS. 2A-B show dithioate and trithioate version of CTA using 3-chloro-2-butanone based R group.
Figure 2B:
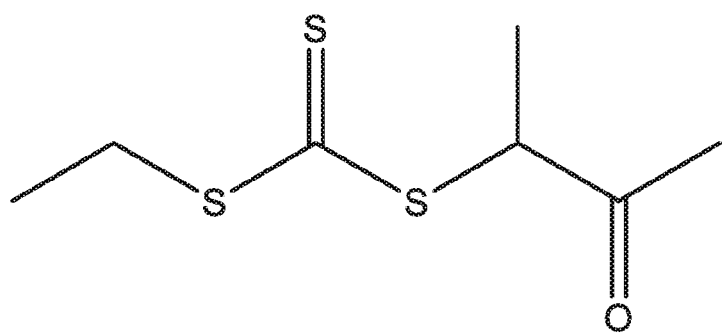

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "aryl" means an aromatic monocyclic or multi-cyclic (polycyclic) ring system of 6 to about 19 carbon atoms, or of 6 to about 10 carbon atoms. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxopyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "halogen" means fluoro, chloro, bromo, or iodo.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. Likewise, all tautomeric forms are also intended to be included.

One aspect of the present invention relates to a compound having the structure of formula (I):

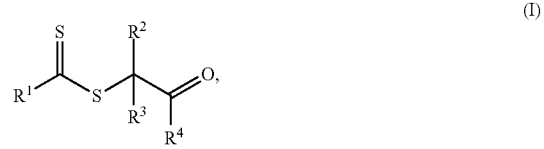

wherein
R$^1$ is aryl or —SC$_{1-20}$ alkyl, wherein the aryl and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H or C$_{1-6}$ alkyl,
R$^6$ is H or C$_{1-6}$ alkyl, and
R$^7$ is H or C$_{1-6}$ alkyl,
with the proviso that when R$^4$ is methyl then R$^1$ is not aryl or —S-t-Bu.

Another aspect of the present invention relates to a compound having the structure of formula (I):

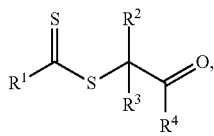

(I)

wherein
R$^1$ is aryl, heteroaryl, heterocyclyl, or —SC$_{1-20}$ alkyl, wherein the aryl, heteroaryl, heterocyclyl, and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H, C$_{1-6}$ alkyl, or —C(O)—(CH$_2$) n-COOH,
R$^6$ is H or C$_{1-6}$ alkyl,
R$^7$ is H or C$_{1-6}$ alkyl, and
n is 1, 2, 3, 4, 5, or 6,
with the proviso that when R$^4$ is methyl then R$^1$ is not aryl or —S-t-Bu.

In one embodiment, the compound is selected from the group consisting of:

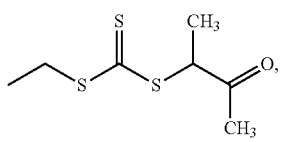

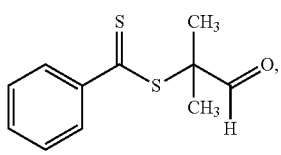

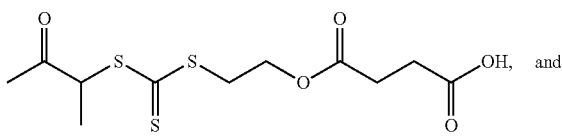 and

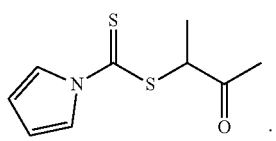

In another embodiment, the compound is selected from the group consisting of:

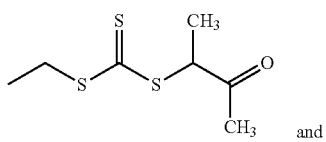 and

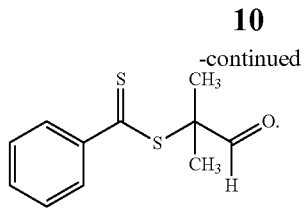

Another aspect of the present invention relates to a process for the preparation of a compound of formula (I):

(I)

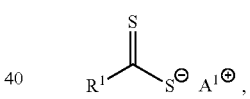

wherein
R$^1$ is aryl or —SC$_{1-20}$ alkyl, wherein the aryl and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H or C$_{1-6}$ alkyl,
R$^6$ is H or C$_{1-6}$ alkyl, and
R$^7$ is H or C$_{1-6}$ alkyl,
with the proviso that when R$^4$ is methyl then R$^1$ is not aryl or —S-t-Bu. The process comprises providing a first intermediate compound of formula (II):

(II)

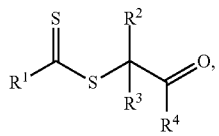

wherein A$^{1\oplus}$ is a suitable cation; and forming the compound of formula (I) from the first intermediate compound of formula (II).

Another aspect of the present invention relates to a process for the preparation of a compound of formula (I):

(I)

wherein
R$^1$ is aryl, heteroaryl, heterocyclyl, or —SC$_{1-20}$ alkyl, wherein the aryl, heteroaryl, heterocyclyl, and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H, C$_{1-6}$ alkyl, or —C(O)—(CH$_2$) n-COOH, $R^6$ is H or $C_{1-6}$ alkyl,
$R^7$ is H or $C_{1-6}$ alkyl, and
n is 1, 2, 3, 4, 5, or 6,
with the proviso that when $R^4$ is methyl then $R^1$ is not aryl or —S-t-Bu. The process comprises providing a first intermediate compound of formula (II):

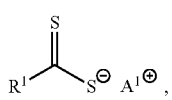

(II)

wherein $A^{1\oplus}$ is a suitable cation; and forming the compound of formula (I) from the first intermediate compound of formula (II).

In one embodiment, $A^{1\oplus}$ is selected from the group consisting of K⁺, Na⁺, Li⁺, triethyl ammonium cation, and piperidinium cation.

In another embodiment, said forming the compound of formula (I) comprises reacting the first intermediate compound of formula (II) with a compound of formula (III):

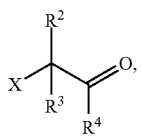

(III)

wherein X is a leaving group, under conditions effective to produce the compound of formula (I).

X can be any suitable leaving group including, but not limited to halogen, —OSO₂R⁹, —OSO₃R⁹, —OCOR⁹, —OCO₂R⁹, —OCSR⁹, —OCS₂R⁹, —OCN(R⁹)₂, —OPO (R⁹)₂, —OPO(OR⁹)₂, and —N(R⁹)₃⁺, wherein R⁹ is selected from the group consisting of hydrogen, $C_1$-$C_6$ alkyl, substituted $C_1$-$C_6$ alkyl, aryl, and substituted aryl.

In one embodiment, X is a halogen. In one example, X is Cl.

In another embodiment, the process further comprises providing a second intermediate compound of formula (IV):

$$R^{1\ominus}A^{2\oplus} \quad (IV),$$

wherein $A^{2\oplus}$ is a suitable cation; and forming the first intermediate compound of formula (II) from the second intermediate compound of formula (IV).

In one embodiment, $A^{2\oplus}$ is selected from the group consisting of K⁺, Na⁺, Li⁺, triethyl ammonium cation, and piperidinium cation.

In a further embodiment, said forming the first intermediate compound of formula (II) comprises reacting the second intermediate compound of formula (IV) with carbon disulfide under conditions effective to produce the first intermediate compound of formula (II).

In another embodiment, the process further comprises providing a compound of formula (V):

$$R^1H \quad (V), \text{ and}$$

reacting the compound of formula (V) with a base to form the second intermediate compound of formula (IV).

In yet another embodiment, the base is selected from the group consisting of K₃PO₄*xH₂O, Na₃PO₄*xH₂O, Li₃PO₄, NaH, Et₃N, piperidine, morpholine, alkali hydroxides; and wherein x is 0 to 10. In one example, the base is K₃PO₄*3H₂O.

The term "alkali hydroxides" refers to compounds composed of alkali metal cation and hydroxyl anion. The alkali metal can be selected from the group consisting of lithium (Li), sodium (Na), potassium (K), rubidium (Rb), caesium (Cs), and francium (Fr). Preferred alkali hydroxides include NaOH, LiOH, and KOH.

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents and different reaction conditions (e.g., temperature, solvent, concentration, etc.)

In accordance with one embodiment of the present invention, Schemes 1-3 below show the preparation of the compounds of the present invention.

Scheme 1

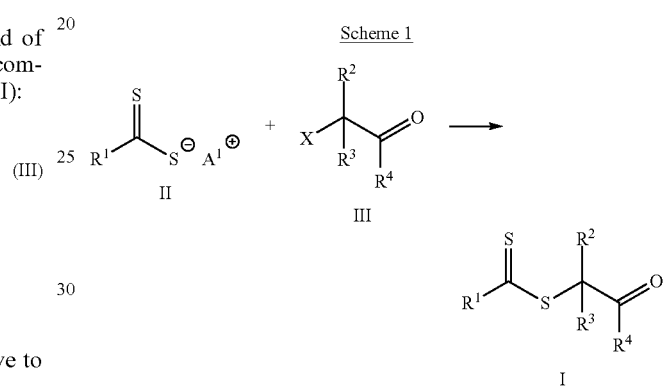

Scheme 2

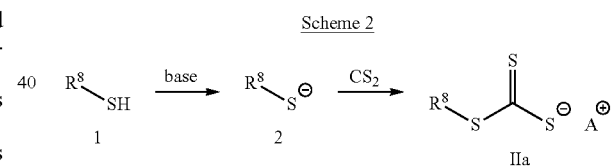

Scheme 3

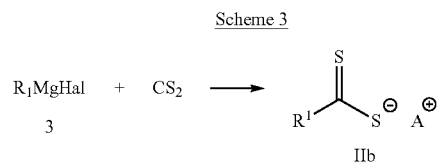

Compounds of formulae III and IIa or IIb are reacted to produce the compound of formula I. In one embodiment, X is a halogen. However, X can be any other suitable leaving group, such as sulfonate ester, sulfate ester, carbonate, thioester, xanthate ester, amide, phosphate ester, phosphonate ester, trialkylammonium, etc. (see also definition of X herein). This reaction can be carried out in any suitable solvent or mixture of the solvents, such as acetone, diethyl ether, or a water/acetone mixture. The reaction is carried out at about −20° C. to about 100° C., preferably, at about −5° C. to about 60° C.

Compounds of formula I wherein $R^1$ is —S—R⁸ can be prepared in accordance with Scheme 2 above. Thiol 1 is reacted with the base to produce thiolate 2. In one embodiment, the base is potassium phosphate tribasic. In another embodiment, the base is sodium hydroxide. This reaction can be carried out in any suitable solvent or mixture of the solvents. In one embodiment, the solvent is acetone. In another embodiment, the solvent is a water/acetone mixture. The reaction is carried out at about −20° C. to about 50° C., preferably, at about −5° C. to about 40° C. The compound of formula 2 is then reacted with carbon disulphide to produce the compound of formula IIa. This reaction can be carried out in any suitable solvent or mixture of the solvents, for example acetone or water/acetone mixture. The reaction is carried out at about 0° C. to about 80° C., preferably, at about 5° C. to about 60° C.

Compounds of formula I wherein $R^1$ is aryl can be prepared in accordance with Scheme 3 above. The compound of formula 3 is reacted with carbon disulfide to produce the compound of formula IIb. In one embodiment, Hal is a chloride. This reaction can be carried out in any suitable solvent or mixture of the solvents, for example in diethyl ether. The reaction is carried out at about −20° C. to about 50° C., preferably, at about −5° C. to about 30° C.

Another aspect of the present invention relates to a process for the synthesis of a polymer. This process comprises providing a monomer composition; providing a chain transfer agent of formula (I):

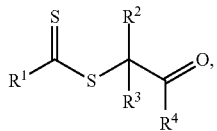

(I)

wherein $R^1$ is aryl or —$SC_{1-20}$ alkyl, wherein aryl and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl; and polymerizing the monomer composition through controlled free radical polymerization with the chain transfer agent to form the polymer.

Another aspect of the present invention relates to a process for the synthesis of a polymer. This process comprises providing a monomer composition; providing a chain transfer agent of formula (I):

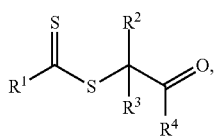

(I)

wherein $R^1$ is aryl, heteroaryl, heterocyclyl, or —$SC_{1-20}$ alkyl, wherein the aryl, heteroaryl, heterocyclyl, and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H, $C_{1-6}$ alkyl, or —C(O)—(CH$_2$) n-COOH,
$R^6$ is H or $C_{1-6}$ alkyl,
$R^7$ is H or $C_{1-6}$ alkyl, and
n is 1, 2, 3, 4, 5, or 6, and polymerizing the monomer composition through controlled free radical polymerization with the chain transfer agent to form the polymer.

The above description of the chain transfer agents of the present invention is fully applicable to the process of using it to form a polymer.

In one embodiment, the chain transfer agent has formula (I):

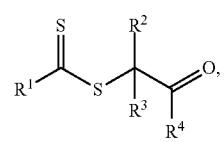

(I)

wherein $R^1$ is aryl or —$SC_{1-20}$ alkyl, wherein aryl and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl, with the proviso that when $R^4$ is methyl then $R^1$ is not aryl or —S-t-Bu.

In another embodiment, the chain transfer agent has formula (I):

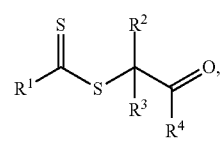

(I)

wherein $R^1$ is aryl, heteroaryl, heterocyclyl, or —$SC_{1-20}$ alkyl, wherein the aryl, heteroaryl, heterocyclyl, and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl,
$R^3$ is H or $C_{1-6}$ alkyl,
$R^4$ is H or $C_{1-6}$ alkyl,
$R^5$ is H, $C_{1-6}$ alkyl, or —C(O)—(CH$_2$) n-COOH, $R^6$ is H or $C_{1-6}$ alkyl,
$R^7$ is H or $C_{1-6}$ alkyl, and
n is 1, 2, 3, 4, 5, or 6, and
with the proviso that when $R^4$ is methyl then $R^1$ is not aryl or —S-t-Bu.

In another embodiment, the chain transfer agent is selected from the group consisting of:

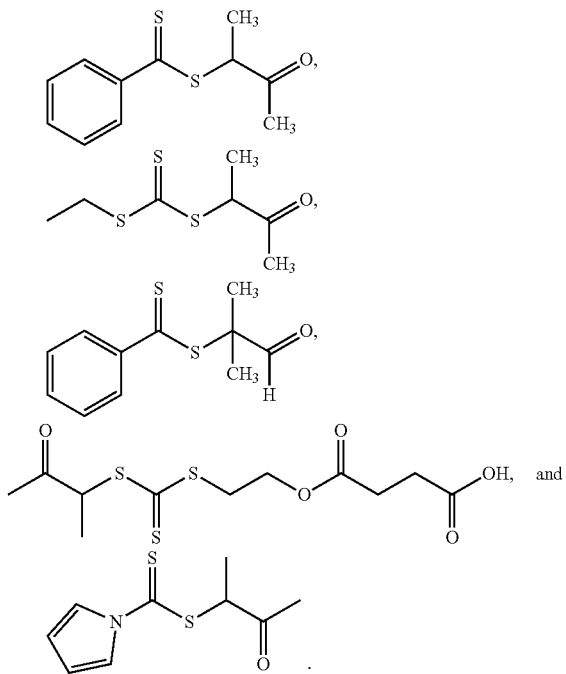

In yet another embodiment, the chain transfer agent is selected from the group consisting of:

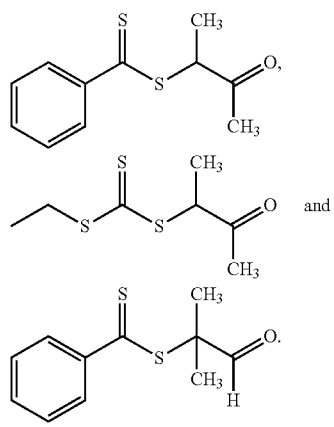

The monomer composition according to the present invention can include one or more monomers. Monomers that can be used according to the present invention include, but are not limited to, a variety type of monomers such as vinyl (such as vinyl aromatic), acrylic (such as methacrylates, acrylates, methacrylamides, acrylamides, etc.), diolefin, nitrile, dinitrile, acrylonitrile monomer, a monomer with reactive functionality, and a crosslinking monomer.

Vinyl aromatic monomers are exemplary vinyl monomers, and include any vinyl aromatics optionally having one or more substituents on the aromatic moiety. The aromatic moiety can be either mono- or polycyclic. Exemplary vinyl aromatic monomers include styrene, α-methyl styrene, t-butyl styrene, vinyl xylene, vinyl naphthalene, vinyl pyridine, divinyl benzene, N-vinyl heteroaromatics (such as 4-vinylimidazole (Vim), N-vinylcarbazole (NVC), N-vinylpyrrolidone, etc.). Other exemplary vinyls include vinyl esters (such as vinyl acetate (VAc), vinyl butyrate (VB), vinyl benzoate (VBz)), N-vinyl amides and imides (such as N-vinylcaprolactam (NVCL), N-vinylpyrrolidone (NVP), N-vinylphthalimide (NVPI), etc.), vinylsulfonates (such as 1-butyl ethenesulfonate (BES), neopentyl ethenesulfonate (NES), etc.), vinylphosphonic acid (VPA), haloolefins (such as vinylidene fluoride (VF2)), etc. Exemplary methacrylates include $C_1$-$C_6$ (meth)acrylate (i.e., methyl methacrylate, ethyl methacrylate, propyl (meth)acrylate, butyl (meth)acrylate, isobutyl methacrylate, heptyl (meth)acrylate, or hexyl (meth)acrylate), 2-(acetoacetoxy)ethyl methacrylate (AAEMA), 2-aminoethyl methacrylate (hydrochloride) (AEMA), allyl methacrylate (AMA), cholesteryl methacrylate (CMA), t-butyldimethylsilyl methacrylate (BDSMA), (diethylene glycol monomethyl ether) methacrylate (DEGMA), 2-(dimethylamino)ethyl methacrylate (DMAEMA), (ethylene glycol monomethyl ether) methacrylate (EGMA), 2-hydroxyethyl methacrylate (HEMA), dodecyl methacrylate (LMA), methacryloyloxyethyl phosphorylcholine (MPC), (poly(ethylene glycol) monomethyl ether) methacrylate (PEGMA), pentafluorophenyl methacrylate (PFPMA), 2-(trimethylamonium)ethyl methacrylate (TMAEMA), 3-(trimethylamonium)propyl methacrylate (TMAPMA), triphenylmethyl methacrylate (TPMMA), etc. Other exemplary acrylates include 2-(acryloyloxy) ethyl phosphate (AEP), butyl acrylate (BA), 3-chloropropyl acrylate (CPA), dodecyl acrylate (DA), di(ethylene glycol) 2-ethylhexyl ether acrylate (DEHEA), 2-(dimethylamino) ethyl acrylate (DMAEA), ethyl acrylate (EA), ethyl α-acetoxyacrylate (EAA), ethoxyethyl acrylate (EEA), 2-ethylhexyl acrylate (EHA), isobornyl acrylate (iBoA), methyl acrylate (MA), propargyl acrylate (PA), (poly(ethylene glycol) monomethyl ether) acrylate (PEGA), tert-butyl acrylate (tBA), etc. Exemplary methacrylamides include N-(2-aminoethyl)methacrylamide (hydrochloride) (AEMAm) and N-(3-aminopropyl)methacrylamide (hydrochloride) (APMAm), N-(2-(dimethylamino)ethyl)acrylamide (DEAPMAm), N-(3-(dimethylamino)propyl)methacrylamide (hydrochloride) (DMAPMAm), etc. Other exemplary acrylamides include acrylamide (Am) 2-acrylamido-2-methylpropanesulfonic acid sodium salt (AMPS), N-benzylacrylamide (BzAm), N-cyclohexylacrylamide (CHAm), diacetone acrylamide (N-(1,1-dimethyl-3-oxobutyl) acrylamide) (DAAm), N,N-diethylacrylamide (DEAm), N,N-dimethylacrylamide (DMAm), N-(2-(dimethylamino)ethyl) acrylamide (DMAEAm), N-isopropylacrylamide (NIPAm), N-octylacrylamide (OAm), etc. Exemplary nitriles include acrylonitrile, adiponitrile, methacrylonitrile, etc. Exemplary diolefins include butadiene, isoprene, etc.

The radically polymerizable monomers suitable for usage herein also include those monomers with reactive functionality, e.g., a 'clickable' functionality so that when the monomers are incorporated in blocks, these 'clickable' functional groups can be used as a precursor to a polymer brush or copolymerized to provide sites for the attachment of functionality or for crosslinking. Exemplary reactive functionality include functional groups suitable for azide-alkyne 1,3-dipolar cycloaddition, such as azide functionality; "active ester" functional groups that are particular active with primary amine functionality; functional groups with protected thiol, hydrazide or amino functionality; functional groups with isocyanate or isothiocyanate functionality, etc.

The radically polymerizable monomers suitable for usage herein can also include those crosslinking monomers that are typically used both in the synthesis of microgels and polymer networks (see below). The monomers can include degradable crosslinks such as an acetal linkage, or disulfide linkages, resulting in the formation of degradable crosslinks. Exemplary crosslinking monomers diethylene glycol dimethacrylate (DEGDMA), triethylene glycol dimethacrylate (TEGDMA), ethylene glycol dimethacrylate (EGDMA), hexane-1,6-diol diacrylate (HDDA), methylene-bis-acrylamide (MBAm), divinylbenzene (DVB), etc.

A more extensive list of exemplary methacrylate monomers, acrylate monomers, methacrylamide monomers, acrylamide monomers, styrenic monomers, diene monomers, vinyl monomers, monomers with reactive functionality, and crosslinking monomers that are suitable for usage as the radically polymerizable monomers herein has been described in Moad et al., "Living Radical Polymerization by the Raft Process—a Third Update," *Australian Journal of Chemistry* 65: 985-1076 (2012), which is hereby incorporated by reference in its entirety.

In one embodiment, the at least one monomer is selected from the group consisting of vinyl aromatics and acrylate.

In a preferred embodiment, the at least one monomer is selected from the group consisting of styrene, butyl acrylate, methyl acrylate, and methyl methacrylate.

The polymerizing step is performed through controlled free radical polymerization which involves living/controlled polymerization with free radical as the active polymer chain end (Moad et al., "The Chemistry of Radical Polymerization—Second Fully Revised Edition," Elsevier Science Ltd. (2006), which is hereby incorporated by reference in its entirety). This form of polymerization is a form of addition polymerization where the ability of a growing polymer chain to terminate has been removed. The rate of chain initiation is thus much larger than the rate of chain propagation. The result is that the polymer chains grow at a more constant rate than seen in traditional chain polymerization and their lengths remain very similar. The polymerizing step typically occurs in the presence of a free radical initiator, and a catalyst or a chain transfer agent to form the polymer.

One form of controlled free radical polymerization is Radical Addition-Fragmentation Chain Transfer (RAFT). Radical Addition-Fragmentation Chain Transfer (RAFT) polymerization is a type of living polymerization or controlled polymerization, utilizing a chain transfer agent (CTA). Conventional RAFT polymerization mechanism, consisting of a sequence of addition-fragmentation equilibria, is shown in Moad et al., "Living Radical Polymerization by the Raft Process—a First Update," *Australian Journal of Chemistry* 59: 669-92 (2006), which is incorporated herein by reference in its entirety. The RAFT polymerization reaction starts with initiation. Initiation is accomplished by adding an agent capable of decomposing to form free radicals; the decomposed free radical fragment of the initiator attacks a monomer yielding a propagating radical ($P_n$), in which additional monomers are added producing a growing polymer chain. In the propagation step, the propagating radical ($P_n$) adds to a chain transfer agent (CTA), followed by the fragmentation of the intermediate radical forming a dormant polymer chain and a new radical (R.). This radical (R.) reacts with a new monomer molecule forming a new propagating radical ($P_m$). In the chain propagation step, ($P_n$) and ($P_m$) reach equilibrium and the dormant polymer chain provides an equal probability to all polymer chains to grow at the same rate, allowing polymers to be synthesized with narrow polydispersity. Termination is limited in RAFT, and, if it occurs, it is negligible. Targeting a specific molecular weight in RAFT can be calculated by multiplying the ratio of monomer consumed to the concentration of CTA used by the molecular weight of the monomer.

The initiating agents often are referred to as "initiators." Suitable initiators depend greatly on the details of the polymerization, including the types of monomers being used, the type of catalyst system, the solvent system, and the reaction conditions. A typical radical initiator can be azo compounds, which provide a two-carbon centered radical. Radical initiators such as benzoyl peroxide, azobisisobutyronitrile (AIBN), 1,1' azobis(cyclohexanecarbonitrile) (ABCN), or 4,4'-Azobis(4-cyanovaleric acid) (ACVA); redox initiator such as benzoyl peroxide/N,N-dimethylaniline; microwave heating initiator; photoinitiator such as (2,4,6-trimethylbenzoyl)-diphenylphosphine oxide; gamma radiation initiator; or Lewis acids such as scandium(III) triflate or yttrium (III) triflate, are typically used in RAFT polymerization.

More details for selection of initiators and reaction conditions for RAFT reaction as well as detailed descriptions for RAFT polymerization can be found in U.S. Patent Application Publication No. 2014/0343192 A1 to Cochran et al., which is hereby incorporated by reference in its entirety.

In one embodiment, the polymerizing is carried out by reversible addition-fragmentation chain-transfer polymerization (RAFT), in the presence of a free radical initiator and a solvent.

In RAFT polymerization, reaction time, temperature, and solvent concentration should be chosen appropriately to ensure the production of non-crosslinked elastomers. Reaction time relates closely to the temperature the reaction is carried out at: higher temperature requires shorter reaction times and lower temperature requires longer reaction times.

Temperatures for the RAFT polymerization can range from room temperature to up to 300° C. The optimal temperature is the minimum at which polymerization can occur over reasonable time scales, e.g., 6-48 hours. Typical reaction temperatures for a RAFT reaction is 250° C. or lower, for instance, from 0 to 250° C., from 50 to 220° C., from 80 to 200° C., from 40 to 100° C., from 50 to 85° C., or from 0 to 50° C. In one embodiment, the polymerizing is carried out at a temperature of 0 to 200° C.

The monomer to CTA ratio can vary depending upon the desired molecular weight. In one embodiment, RAFT polymerization is carried out at a molar ratio of the chain transfer agent to the monomer ranging from 1:1 to 1:10000.

The solvent is selected based the requirements of monomer solubility and a normal boiling point compatible with the polymerization temperature. The solvent used in the RAFT polymerization may be toluene, dioxane, THF, chloroform, cyclohexane, dimethyl sulfoxide, dimethyl formamide, acetone, acetonitrile, n-butanol, n-pentanol, chlorobenzene, dichloromethane, diethylether, tert-butanol, 1,2,-dichloroethylene, diisopropylether, ethanol, ethylacetate, ethylmethylketone, heptane, hexane, isopropylalcohol, isoamylalcohol, methanol, pentane, n-propylalcohol, pentachloroethane, 1,1,2,2,-tetrachloroethane, 1,1,1,-trichloroethane, tetrachloroethylene, tetrachloromethane, trichloroethylene, water, xylene, benzene, nitromethane, glycerol, or a mixture thereof.

The solvent can further include stabilizers, surfactants, or dispersants.

The concentrations of the monomer used in the reactions depend partially on the solubility of the monomer and the polymer products as well as the evaporation temperature of the solvent. Solvent concentration can affect the gelation of the polymer. Insufficient solvent in the RAFT reaction can cause the polymer to crosslink in a shorter time period without ever reaching high enough conversions. Therefore, the solvent is typically added in excess to allow the polymer chains to grow and obtain a conversion rate to 80% without risk of the polymer reaching the gel point. The concentration of the monomer dissolved in the solvent in the RAFT reactions may range from 1% to 100% weight percentage monomer. Typically, a monomer concentration of less than 90 wt % is suitable to ensure the solubility of the resulting polymers and additionally to prevent premature gelation.

In one embodiment, the method is carried out in the presence of a solvent, with the monomer having a concentration, when dissolved in the solvent, ranging from 1 wt % to 90 wt %, for instance, from 1 wt % to 40 wt %, from 1 wt % to 10 wt %, or from 20 wt % to 30 wt %.

In one embodiment, RAFT polymerization of the monomer is carried out with a free radical initiator selected from the group consisting of benzoyl peroxide and azobisisobutyronitrile.

The polymer produced by the process according to the third aspect of the present invention can be a homopolymer, copolymer, block copolymer, or statistical copolymer. In one embodiment, the polymer is a multi block copolymer.

In another embodiment, the polydispersity index (DPI) of the polymer is less than 2. Alternatively, the polydispersity index (DPI) of the polymer is less than 1.5. As a further alternative, the polydispersity index (DPI) of the polymer is less than 1.2.

In another embodiment, the chain transfer agent having the structure of Formula (I) is supported on an inert carrier. The inert carrier can be a porous solid selected from the group consisting of talc, a sheet silicate, an inorganic oxide, and a finely divided polymer powder.

In another embodiment, polymerizing is carried out to produce the homopolymer, copolymer, or block copolymer having a linear or branched-chain structure. Such polymerizing can be carried out under conditions effective to produce the homopolymer, copolymer, or block copolymer with a molecular weight of at least 1 KDa without gelation. In another embodiments, polymerizing is carried out to produce thermoplastic block copolymer.

In a further embodiment, the process also includes providing a radically polymerizable monomer and polymerizing the radically polymerizable monomer through reversible addition-fragmentation chain-transfer polymerization (RAFT) with the thermoplastic block copolymer as a macromolecular chain transfer agent to add an additional block to the block copolymer.

The homopolymer, copolymer, or block copolymer, when containing unreacted acrylated groups, can undergo a crosslinking reaction at an elevated temperature. The homopolymer, copolymer, or block copolymer can be further chemically modified with a crosslinking agent, allowing the homopolymer, copolymer, or block copolymer to undergo a crosslinking reaction at an elevated temperature.

The crosslinking agent used to chemically modify the homopolymer, copolymer, or block copolymer can include those that are typically used both in the synthesis of microgels and polymer networks, e.g., degradable crosslinks such as an acetal linkage, or disulfide linkages, resulting in the formation of degradable crosslinks. Exemplary crosslinking agents used to modify the homopolymer, copolymer, or block copolymer include diethyleneglycol dimethacrylate (DEGDMA), diethylene glycol diacrylate, triethylene glycol dimethacrylate (TEGDMA), ethyleneglycol dimethacrylate (EGDMA), hexane-1,6-diol diacrylate (HDDA), methylene-bis-acrylamide (MBAm), divinylbenzene (DVB), p-divinylbenzene (p-DVB), sulfur, 1,4-cyclohexanedimethanol divinyl ether, N,N'-(1,2-dihydroxyethylene)bisacrylamide, ethylene glycol diacrylate, ethylene glycol dimethacrylate, 4,4'-methylenebis(cyclohexyl isocyanate), 1,4-phenylene-diacryloyl chloride, poly(ethylene glycol) diacrylate, poly(ethylene glycol) dimethacrylate, tetra(ethylene glycol) diacrylate, tetraethylene glycol dimethyl ether, triethylene glycol dimethacrylate, potassium metaborate, triethanolaminezirconate, sodium tetraborate, boric acid, zirconium complexes, borate salts, methanol, etc.

The homopolymer, copolymer, or block copolymer can be further chemically modified with a reagent to confer an acidic or basic functionality to the homopolymer, copolymer, or block copolymer, making the homopolymer, copolymer, or block copolymer a pH adjusting agent. Unreactive hydroxyl groups in the polyols can be modified with a diacid such as oxalic acid, malonic acid, succinic acid, glutatic acid, adipic acid, pimelic acid, suberic acid, azelaic acid, sebacic acid, undecanoic acid, dodecanoic acid; or a dicarboxylic acid such as ortho-phtalic acid, isophtalic acid, terephthalic acid, to provide an acidic environment. Unreactive hydroxyl groups in the polyols can also be modified with a dibasic salt such as glyphosphate, hydroquinone, resorcinol, to provide a basic environment.

The homopolymer, copolymer, or block copolymer can be further chemically modified with a reagent to confer a biocidic functionality to the homopolymer, copolymer, or block copolymer, making the homopolymer, copolymer, or block copolymer a biocide agent. The reagent can be a quaternary ammonium, glutaraldehyde, tetrakis hydroxymethyl phosphonium sulfate, etc.

In another embodiment, the homopolymer is polystyrene.

The following examples are provided to illustrate embodiments of the present invention, but they are by no means intended to limit the scope.

EXAMPLES

Example 1—Reagents

Phenylmagnesium bromide (PMB) was purchased from Sigma-Aldrich at a 3M concentration in diethyl ether. Carbon disulfide was purchased from Sigma-Aldrich at 99% purity. 3-Chloro-2-butanone was purchased from Sigma-Aldrich at 97% purity. Potassium phosphate was purchased from Fisher Scientific at 97% purity. HPLC grade acetone was purchased from Fisher Scientific. Ethanethiol was purchased from Sigma-Aldrich at 97% purity. Styrene and n-butyl acrylate were purchased from Sigma-Aldrich at 99% purity. Initiators azobisisobutyronitrile (AIBN) and di-tert-butyl peroxide (TBP) were all purchased from Sigma Aldrich.

Example 2—CTA Synthesis

Synthesis of 3-Oxobutan-2-yl Benzodithioate

The synthesis of 3-oxobutan-2-yl benzodithioate (OXBED) is very similar to other dithio based CTA's (Gregory et al., "Controlled Dispersion Polymerization of Methyl Methacrylate in Supercritical Carbon Dioxide via RAFT," *Macromolecules* 41:1215-1222 (2008), which is hereby incorporated by reference in its entirety). It can be synthesized from scratch by producing the Grignard reagent (PMB) or by starting from PMB. As the procedure for making PMB is well known, and it is simple to purchase this molecule which was started from the pre-made PMB.

Phenylmagnesium bromide (1 equivalent) (3M solution in diethyl ether) was added to a round bottom flask. The contents of the flask were cooled down to 0° C. using an ice bath. Next, carbon disulfide ($CS_2$) (1.5 equivalents) was slowly added over the course of 45 minutes. The reaction mixture was allowed to stir for 2 hours before 3-chloro-2-butanone (2 equivalents) was added in. Upon completion of the reaction, water was added to neutralize any remaining Grignard reagent. A separation was done using diethyl ether, and the product was then dried over magnesium sulfate and isolated by rotary evaporation. This yielded 3-oxobutan-2-yl benzodithioate with 95%+ purity and 90%+ yield.

Synthesis of Ethyl (3-Oxobutan-2-yl) Carbonotrithioate

Ethyl (3-oxobutan-2-yl) carbonotrithioate (OXCART) was prepared by taking 1.1 equivalent of potassium phosphate in 13 equivalents of acetone. Ethanethiol (1 equivalent) was then added and the reaction mixture was allowed to stir for ten minutes. Carbon disulfide (1.5 equivalents) was then slowly added over the course of an hour. The reaction mixture was allowed to stir for 10 minutes. Finally, 3-chloro-2-butanone (2 equivalents) was added over the course of a half an hour and the reaction mixture was allowed to stir for 10 minutes. The product was then filtered and the salts were washed with acetone and the solvent, the excess carbon disulfide, and excess 3-chloro-2-butanone were removed under reduced pressure. The product was used without further purification. Ethyl (3-oxobutan-2-yl) carbonotrithioate was obtained with 95%+ purity and 90%+ yield.

Ethyl (3-oxobutan-2-yl) carbonotrithioate was also prepared as described above by using sodium hydroxide as the base and a water/acetone (80/20) mixture as the solvent. The product was isolated by using a liquid extraction instead of filtering and washing. By using this method, ethyl (3-oxobutan-2-yl) carbonotrithioate was obtained with a very high purity (95%+) and yield (90%+).

Example 3—Polymerization

Each molecule was tested with both styrene and n-butyl acrylate to confirm that there was a good RAFT control.

Butyl acrylate was tested at 80° C. and 65° C. for the dithioester and trithiocarbonate, respectively—the temperature difference was due to the substantial difference in kinetics for dithioester and trithio-carbonate. N-butyl acrylate (78 equivalents), CTA (1 equivalent), AIBN (0.3 equivalents), and toluene (added to make a 33 mass % solution) were added to a reaction vial and were bubbled with argon for 15 minutes. After that they were heated to the appropriate temperature and aliquots were taken periodically. Finally, gravometric conversion and gel permeation chromatography (GPC) were used to characterize molecular weight and conversion.

Styrene was tested under a number of different conditions. Traditionally, in literature, it is exceedingly rare to see people test temperatures above 100° C. Also, it is common to use AIBN regardless of temperature. This seems to be a mistake as the 10 hour half life of AIBN is 65° C. TBP has a 10 hour half life above AIBN and should show superior results and so we showed data under these improved conditions.

Kinetic data was collected for styrene at 100° C. using AIBN as the initiator in bulk. Kinetic data was also collected for polymerization of styrene at 125° C. and 135° C. using TBP as the initiator and at 50% solids in cyclohexane.

Example 4—Results & Data

CTA Synthesis

Figure 3:
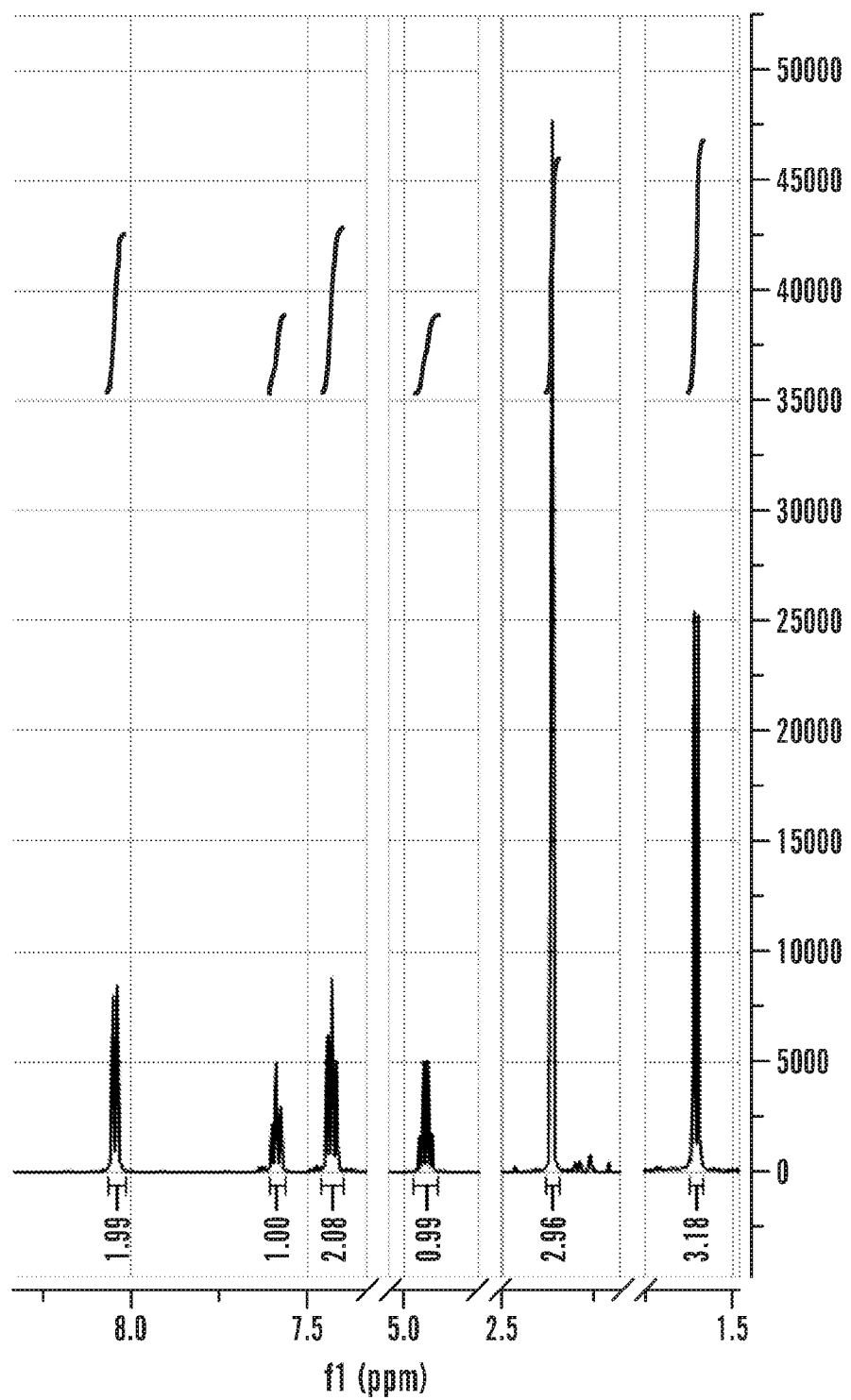
FIG. 3 shows proton NMR of 3-oxobutan-2-yl benzodithioate.
Figure 4:
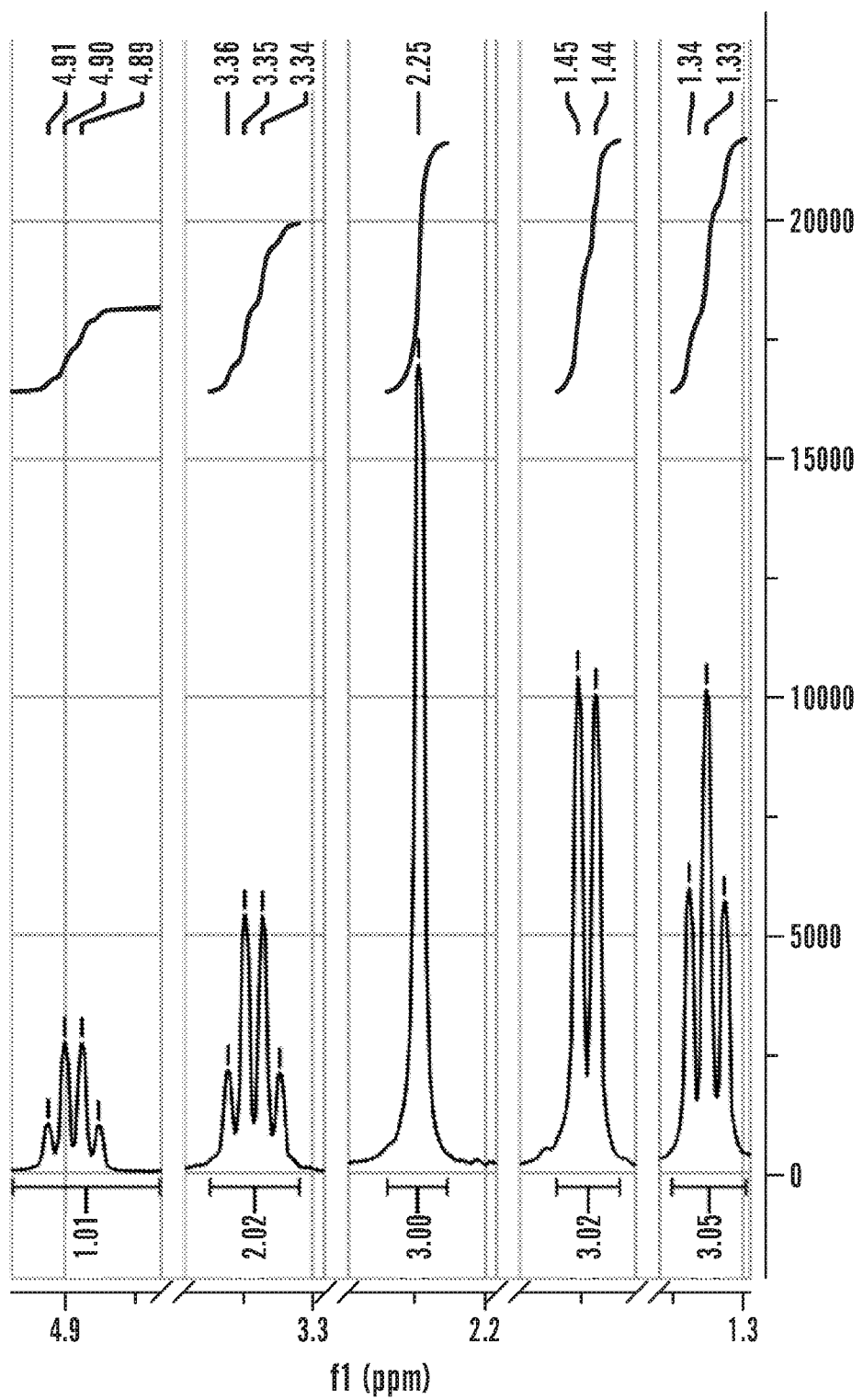
FIG. 4 shows proton NMR of ethyl (3-oxobutan-2-yl) carbonotrithioate.

Proton NMR with a 600 MHz Bruker NMR—shown in FIG. 3 and FIG. 4—showed that the synthesis of both the dithioate and trithioate CTA's produced with the R group being based on 3-chloro-2-butanone was extremely clean. The NMR clearly showed that there are very few impurities.

Figure 5:
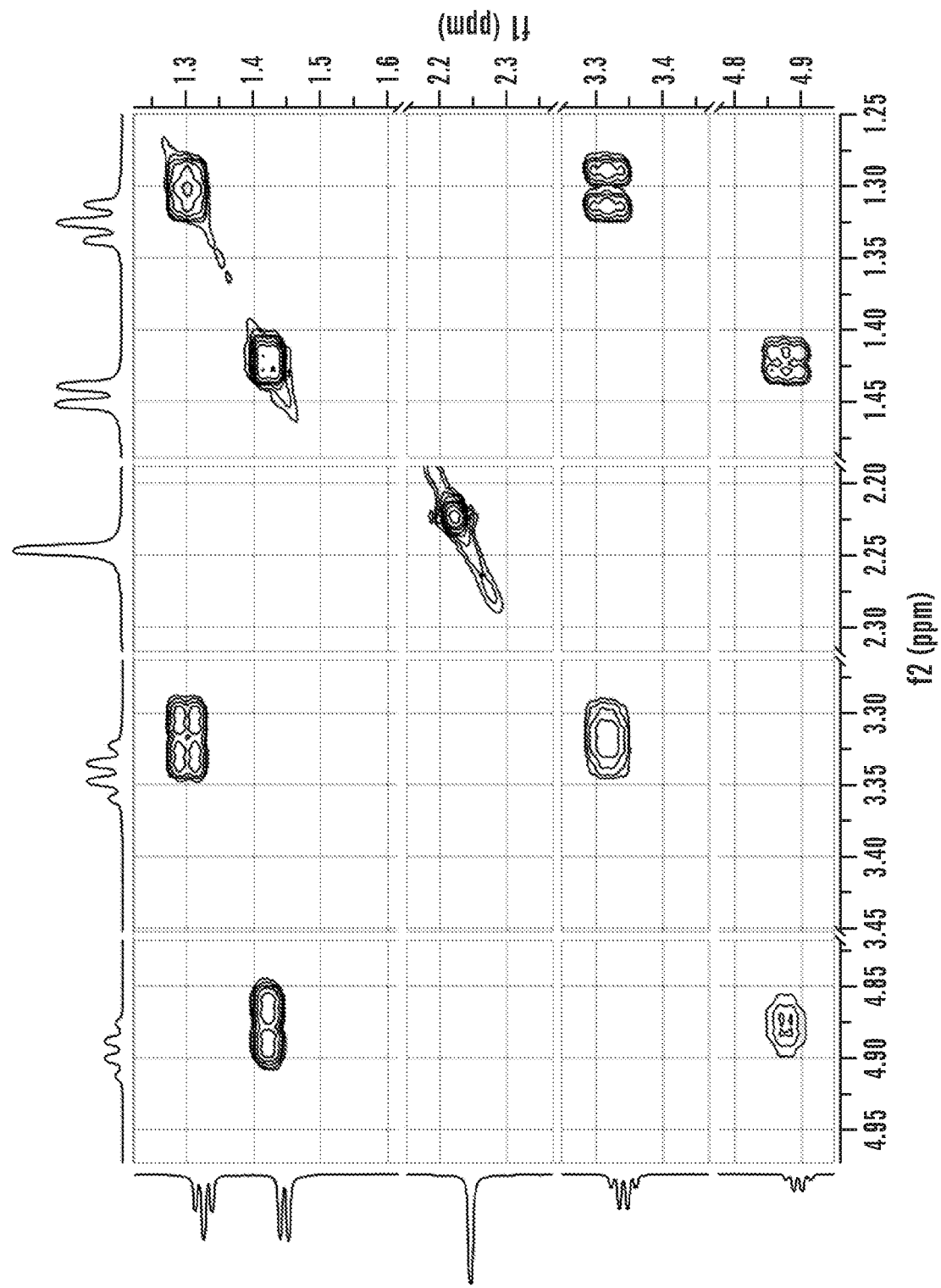
FIG. 5 shows COSY NMR of (3-oxobutan-2-yl) carbonotrithioate.
Figure 6:
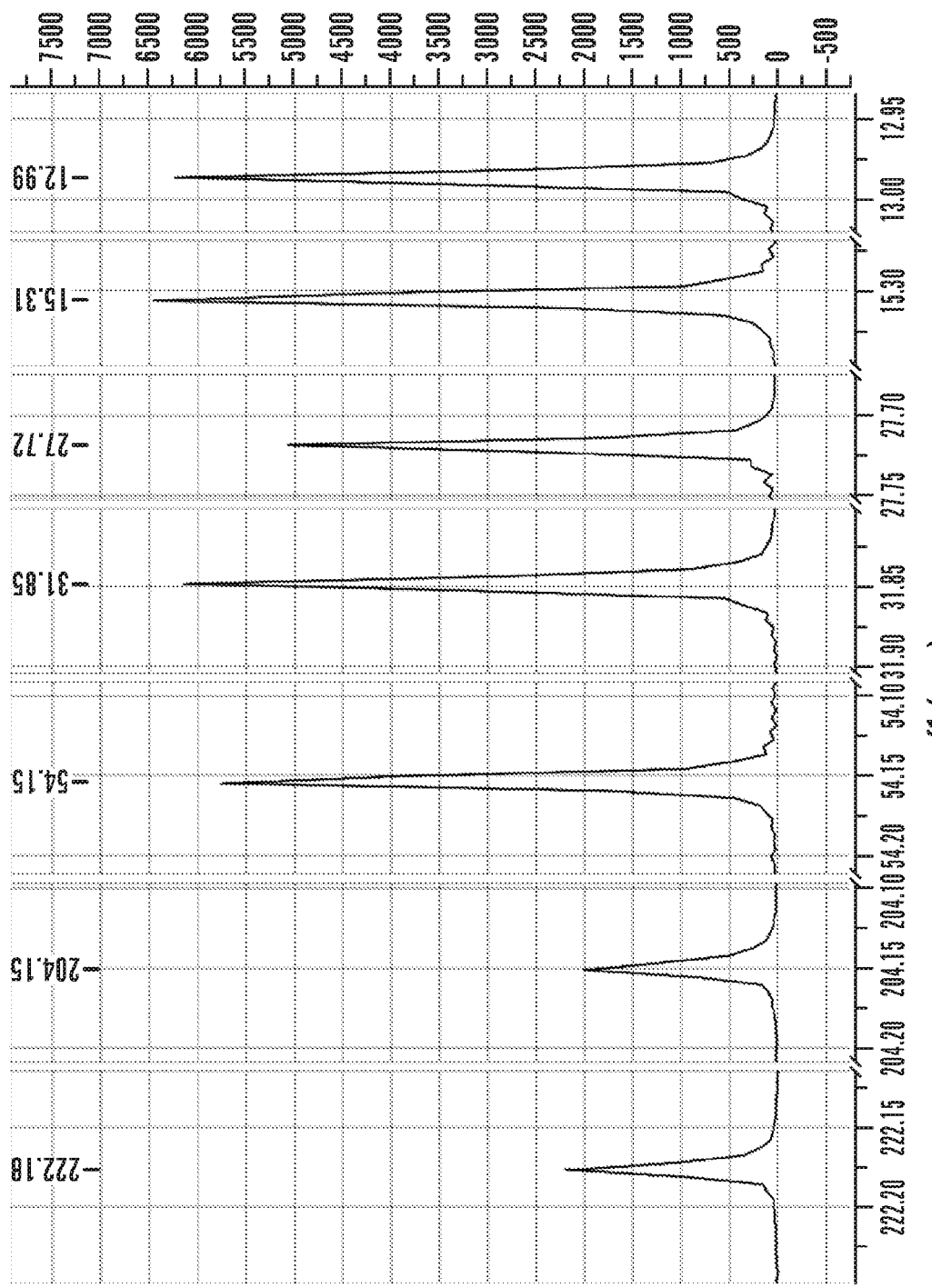
FIG. 6 shows Carbon-NMR of (3-oxobutan-2-yl) carbonotrithioate.
Figure 7:
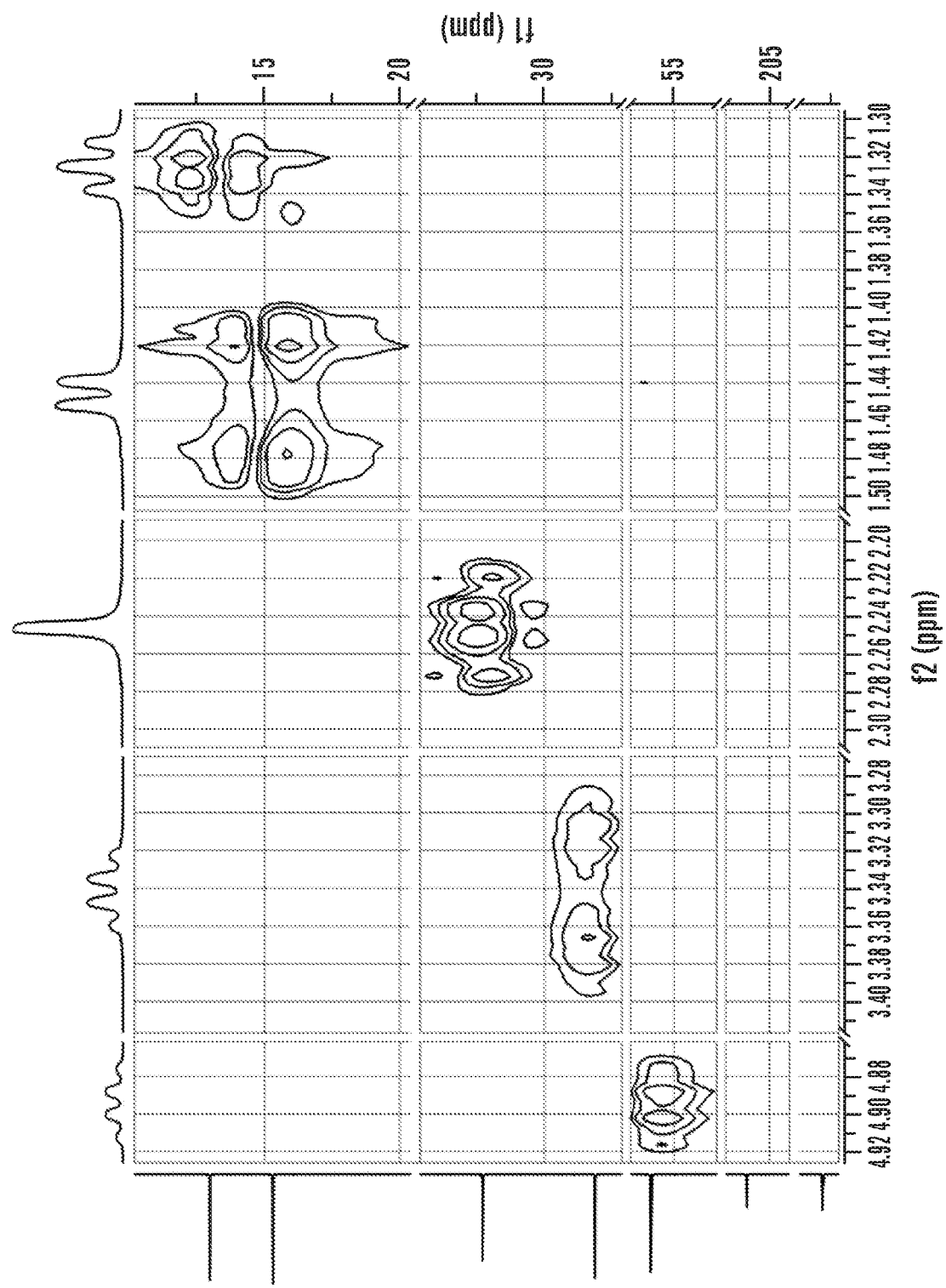
FIG. 7 shows HSQC NMR of (3-oxobutan-2-yl) carbonotrithioate.

Ethyl (3-oxobutan-2-yl) carbonotrithioate was also characterized using COSY NMR, C-NMR, and HSQC NMR. The COSY spectrum (FIG. 5) showed the interaction between the proton in the 2 position and the 1 position. It also showed the interaction of the proton in the 4 position and the 5 position. Carbon Spectra (FIG. 6) also confirmed the structure. Carbon 1-12.99, Carbon 2-31.85, Carbon 3-222.18, Carbon 4-54.15, Carbon 5-15.31, Carbon 6-204.15, Carbon 7-27.72. HSQC (FIG. 7) showed that carbons 1, 2, 4, 5, and 7 match with protons 1, 2, 4, 5, and 7. The combination of these spectra definitively showed that the product that we were looking to make was synthesized.

Polymerization

Figure 8:
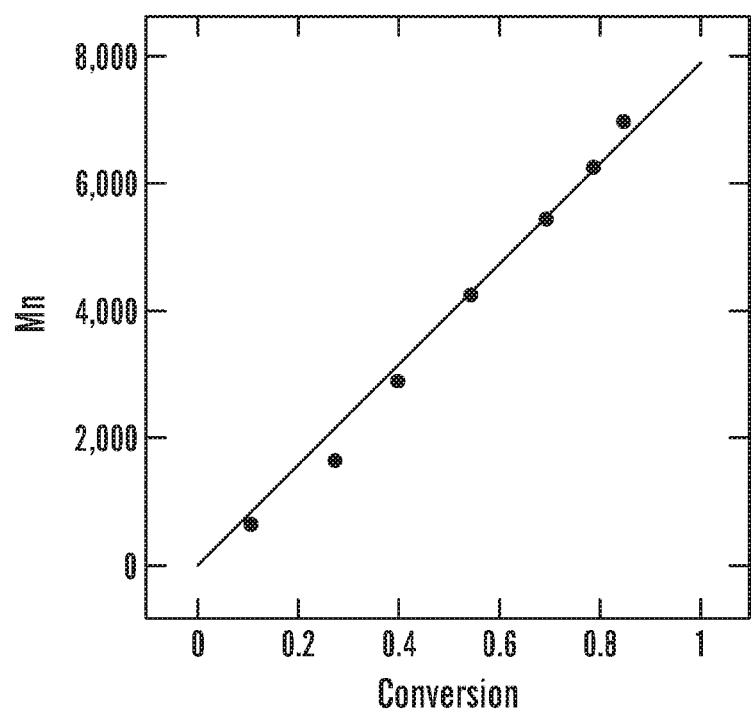
FIG. 8 is a plot of molecular weight versus conversion for butyl acrylate.
Figure 9:
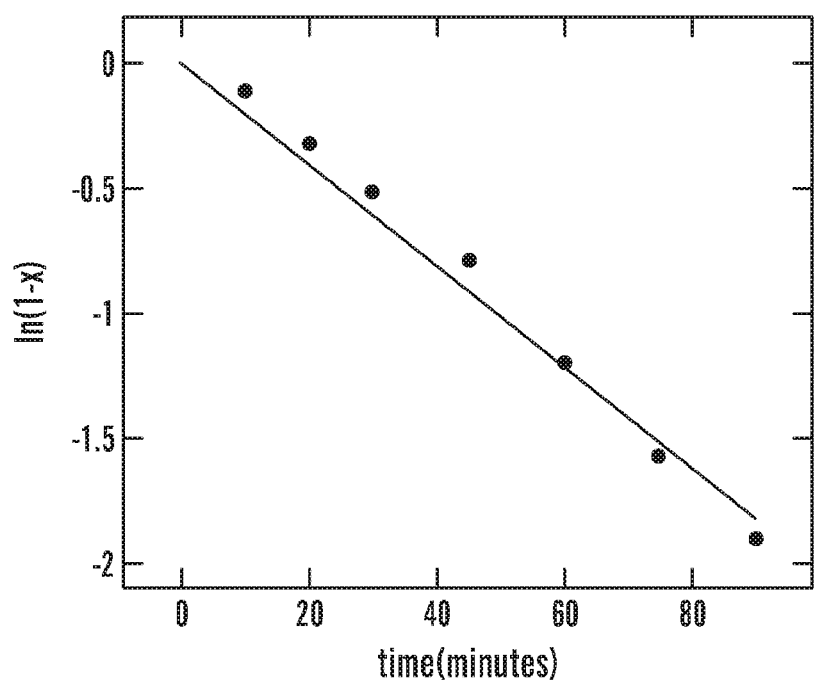
FIG. 9 is a plot of natural log of 1-conversion vs time for butyl acrylate.

The results of polymerization of butyl acrylate using OXCART are shown in FIGS. 8 and 9 and Table 1. As can be seen from FIG. 8, the conversion versus molecular weight was clearly the linear trend that would be expected for good control of RAFT systems. This indicated that OXCART does function as desired for controlling the molecular weights. This was emphasized by the low PDI's shown in Table 1. In addition, the plot of log of conversion versus time showed a nice linear trend as would be expected for a polymerization of butyl acrylate at 65° C. Very high conversions were also observed. After 90 minutes, a conversion of 85% was achieved.

TABLE 1

Polymerization of Butyl Acrylate
Butyl Acrylate Polymerization using OXCART

| Time | Conversion | Mn | PDI |
| --- | --- | --- | --- |
| 10 | 10.9% | 1.5 kDa | 1.18 |
| 20 | 27.55% | 3.0 kDa | 1.21 |
| 30 | 40.1% | 4.637 Da | 1.24 |
| 45 | 54.6% | 6.262 kDa | 1.18 |
| 60 | 69.63% | 7.228 kDa | 1.17 |
| 75 | 79.1% | 7.8 kDa | 1.17 |
| 90 | 85.0% | 8.233 kDa | 1.17 |

Figure 10:
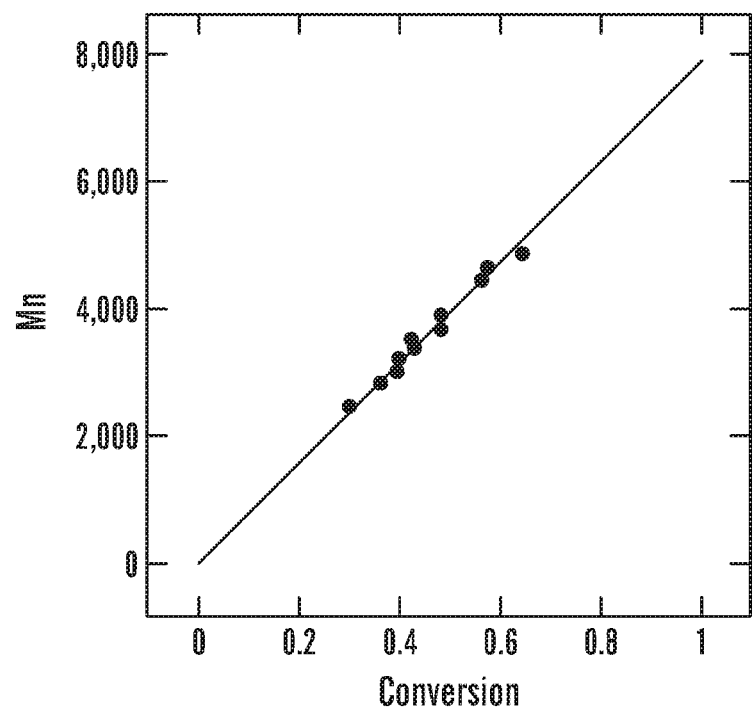
FIG. 10 is a plot of molecular weight versus conversion for styrene at 100° C.
Figure 11:
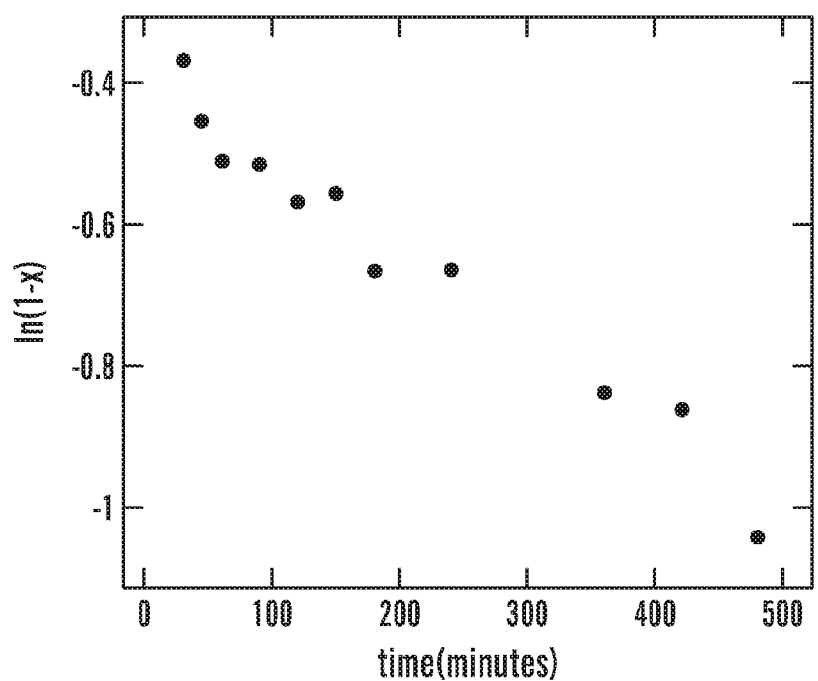
FIG. 11 is a plot of natural log of 1-conversion vs time for styrene at 100° C.
Figure 12:
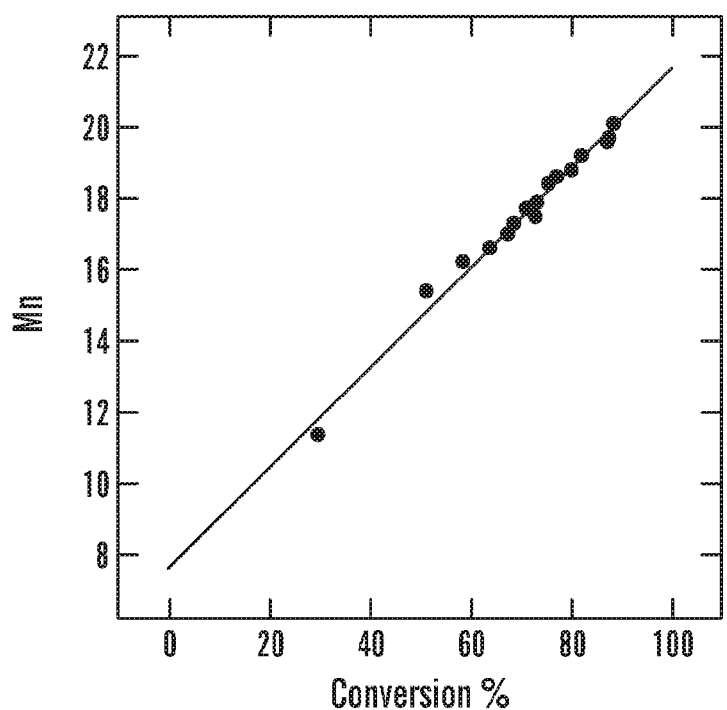
FIG. 12 is a plot of molecular weight versus conversion for styrene at 125° C.
Figure 13:
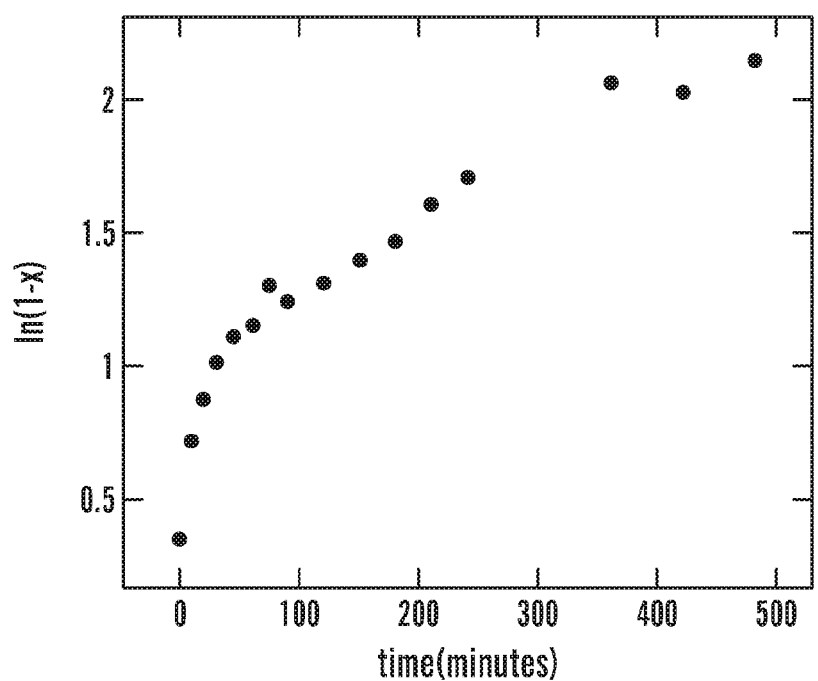
FIG. 13 is a plot of natural log of 1-conversion vs time for styrene at 125° C.
Figure 14:
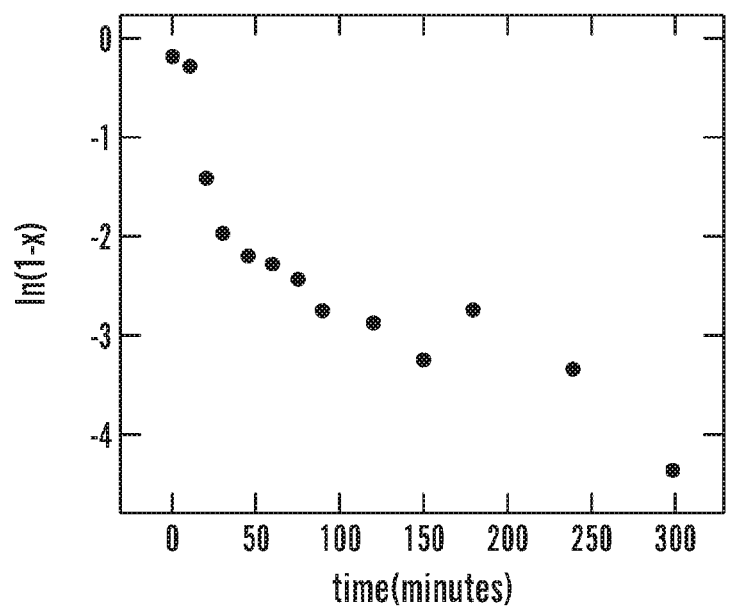
FIG. 14 is a plot of natural log of 1-conversion vs time for styrene at 135° C.
Figure 15:
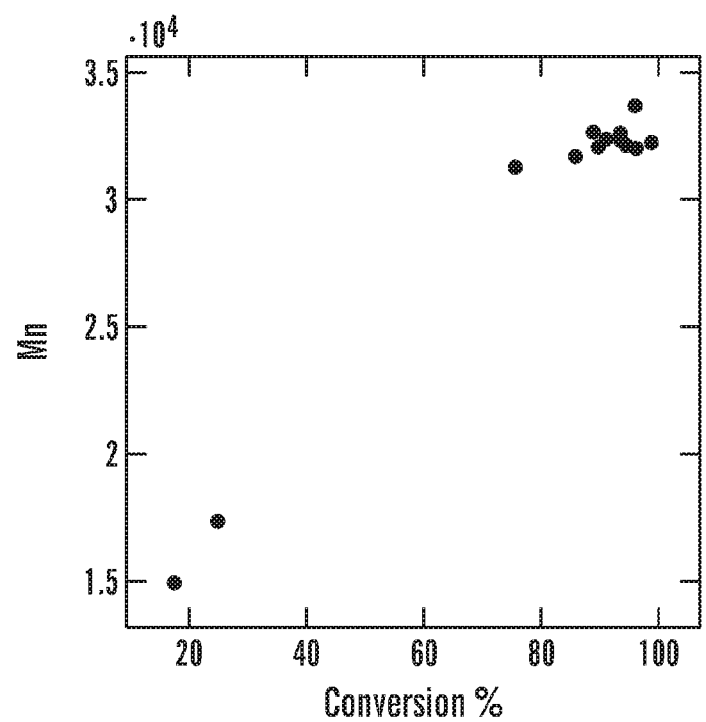
FIG. 15 is a plot of molecular weight versus conversion for styrene at 135° C.

The results of the polymerization of styrene at 100° C. with AIBN as the initiator is shown in FIGS. 10 and 11, and Table 2. While the conversion versus molecular weight plot was very linear, the log of the conversion versus time plot was not. As can be seen from the data, for the first 90 minutes, the slope was linear and fairly steep. Following 90 minutes, the slope was again linear, but much less steep. When the temperature was increased to 125° C., it was found that the reaction cannot be done under bulk conditions as the conversion is high enough to make the stirring of styrene magnetically impossible. At this point, the concentration was decreased to a 50% solids in cyclohexane in order to keep the viscosity under control. As can be seen from FIGS. 12 and 13 and Table 3, increasing the temperature had a substantial effect on the kinetics while did not significantly raising the PDI. When the temperature was raised to 135° C., results shown in FIGS. 14 and 15 and Table 4, the PDI did not substantially rise, but the conversion quickly reached very high values and continued to increase, while the molecular weight did not substantially change. This indicated that perhaps such temperatures were reached that the limits of what the CTA can control were reached. This is further suggested by the high amount of tailing on the low molecular weight side of the GPC curve.

TABLE 2

Polymerization of Styrene at 100° C.
PS Polymerization at 100° C. Results

| Time | Conversion | Mn | PDI |
|---|---|---|---|
| 30 | 30.6% | 2.9 kDa | 1.16 |
| 45 | 36.3% | 3.3 kDa | 1.15 |
| 60 | 49.8% | 3.5 kDa | 1.15 |
| 90 | 40.2% | 3.7 kDa | 1.14 |
| 120 | 43.3% | 3.9 kDa | 1.14 |
| 150 | 42.6% | 4.0 kDa | 1.14 |
| 180 | 48.6% | 4.2 kDa | 1.14 |
| 240 | 48.5% | 4.4 kDa | 1.13 |
| 360 | 56.7% | 5.0 kDa | 1.12 |
| 420 | 57.8% | 5.2 kDa | 1.11 |
| 480 | 64.8% | 5.4 kDa | 1.11 |

TABLE 3

Polymerization of Styrene at 125° C.
PS Polymerization in CHX at 125° C. Results

| Time | Conversion | Mn | PDI |
|---|---|---|---|
| 0 | 30% | 11.4 kDa | 1.26 |
| 10 | 51.4% | 15.4 kDa | 1.25 |
| 20 | 58.5% | 16.2 kDa | 1.24 |
| 30 | 63.9% | 16.6 kDa | 1.22 |
| 45 | 67.3% | 17.0 kDa | 1.22 |
| 60 | 68.5% | 17.3 kDa | 1.22 |
| 75 | 72.8% | 17.5 kDa | 1.22 |
| 90 | 71.1% | 17.7 kDa | 1.22 |
| 120 | 73.2% | 17.9 kDa | 1.22 |
| 150 | 75.4% | 18.4 kDa | 1.22 |
| 180 | 77.0% | 18.6 kDa | 1.22 |
| 210 | 80.0% | 18.8 kDa | 1.22 |
| 240 | 81.9% | 19.2 kDa | 1.21 |
| 360 | 87.3% | 19.7 kDa | 1.21 |
| 420 | 86.8% | 19.6 kDa | 1.22 |
| 480 | 88.3% | 20.1 kDa | 1.21 |

TABLE 4

Polymerization of Styrene at 135° C.
PS Polymerization at 135° C. Results

| Time | Conversion | Mn | PDI |
|---|---|---|---|
| 0 | 17.19114688 | 14970.92 | 1.309712 |
| 10 | 24.72553699 | 17401.76 | 1.297842 |
| 20 | 75.57027922 | 31256.77 | 1.236652 |
| 30 | 85.91439689 | 31704.97 | 1.242584 |
| 45 | 88.88132709 | 32676.63 | 1.242247 |
| 60 | 89.6744186 | 32053.11 | 1.25392 |
| 75 | 91.10732538 | 32420.64 | 1.242884 |
| 90 | 93.52472089 | 32637.69 | 1.248643 |
| 120 | 94.27991886 | 32129.77 | 1.249307 |
| 150 | 96.06299213 | 33705.23 | 1.35986 |
| 180 | 93.54166667 | 32316.44 | 1.246105 |
| 240 | 96.42761693 | 32050.81 | 1.252594 |

TABLE 4-continued

Polymerization of Styrene at 135° C.
PS Polymerization at 135° C. Results

| Time | Conversion | Mn | PDI |
|---|---|---|---|
| 300 | 98.69879518 | 32243.11 | 1.246624 |
| 360 | 106.557377 | 32733.34 | 1.252941 |
| 420 | 104.8698315 | 32133.56 | 1.255908 |
| 480 | 104.9462366 | 32388.42 | 1.252882 |

Figure 17:
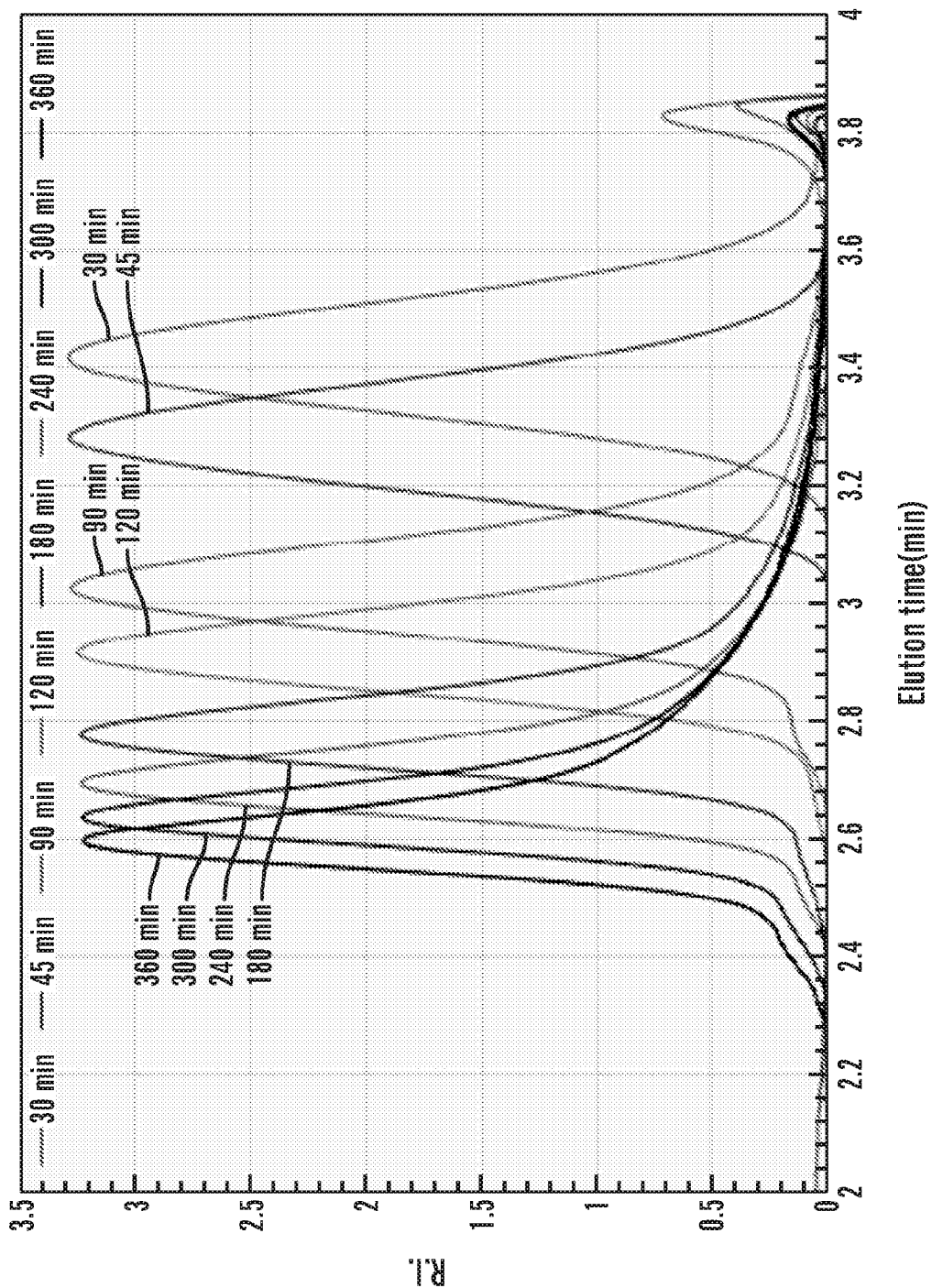
FIG. 17 shows GPC traces of butyl acrylate polymerization with dithioate OXCART (OXBED).
Figure 22:
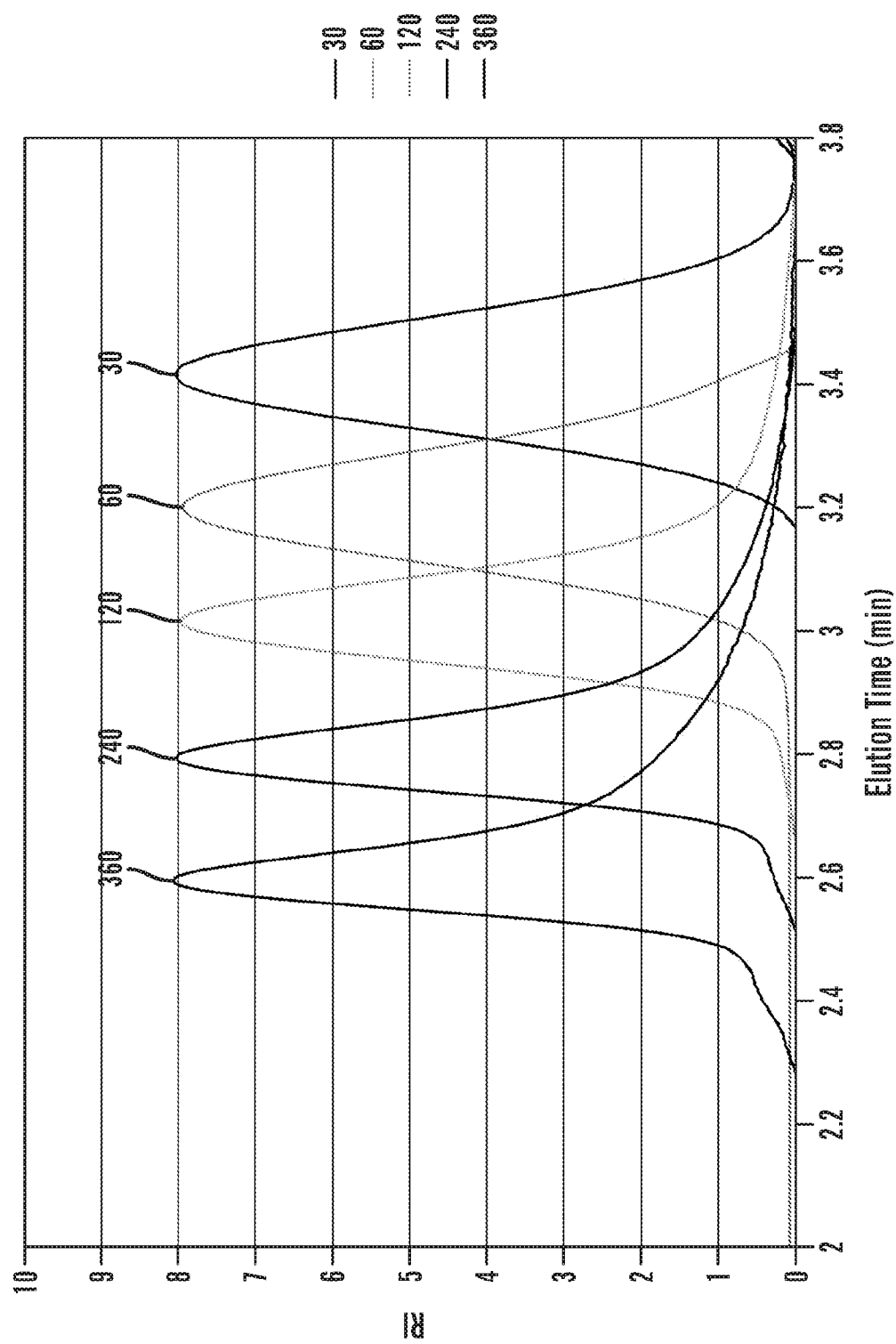
FIG. 22 shows the GPC traces of the polymerization of butyl acrylate using OXBED as the CTA.

The GPC results of polymerization of methyl acrylate and butyl acrylate using OXBED are shown in FIGS. 17 and 22, respectively. As can be seen, the molecular weight increased in a controlled fashion, as expected when the RAFT system is controlled. This indicated that the OXBED CTA does control molecular weights.

Figure 16:
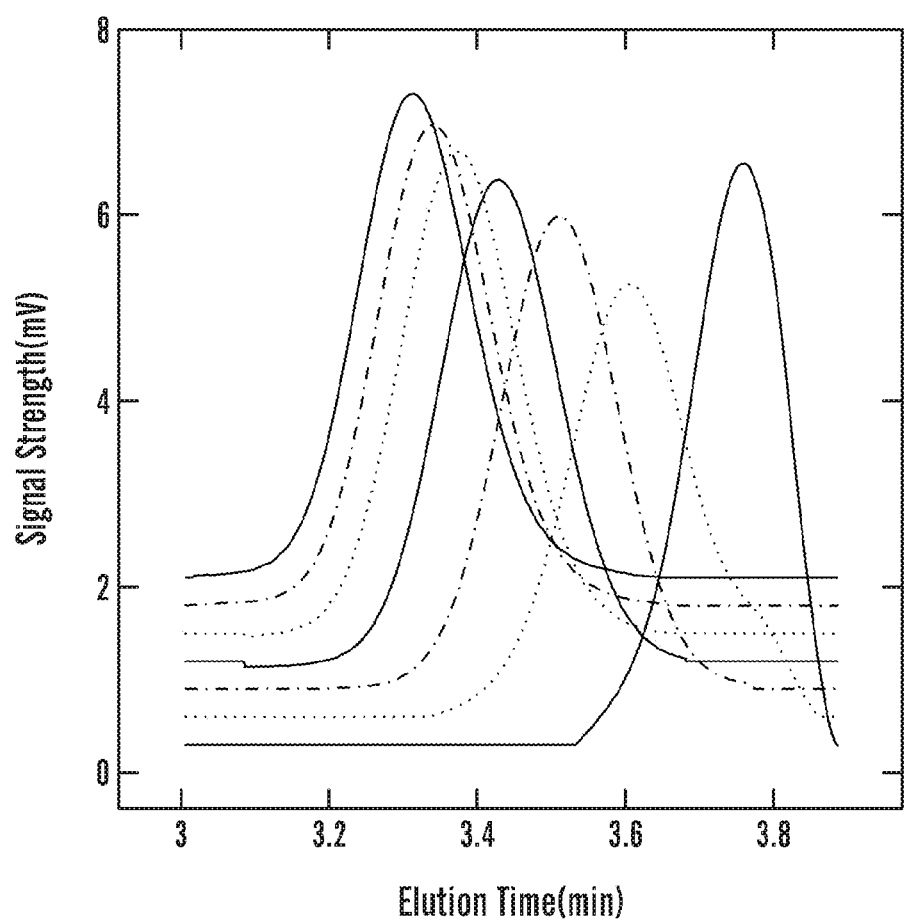
FIG. 16 shows GPC traces of butyl acrylate polymerization with trithioate OXCART.

The GPC results of polymerization of butyl acrylate using trithioate OXCART is shown in FIG. 16.

Figure 18:
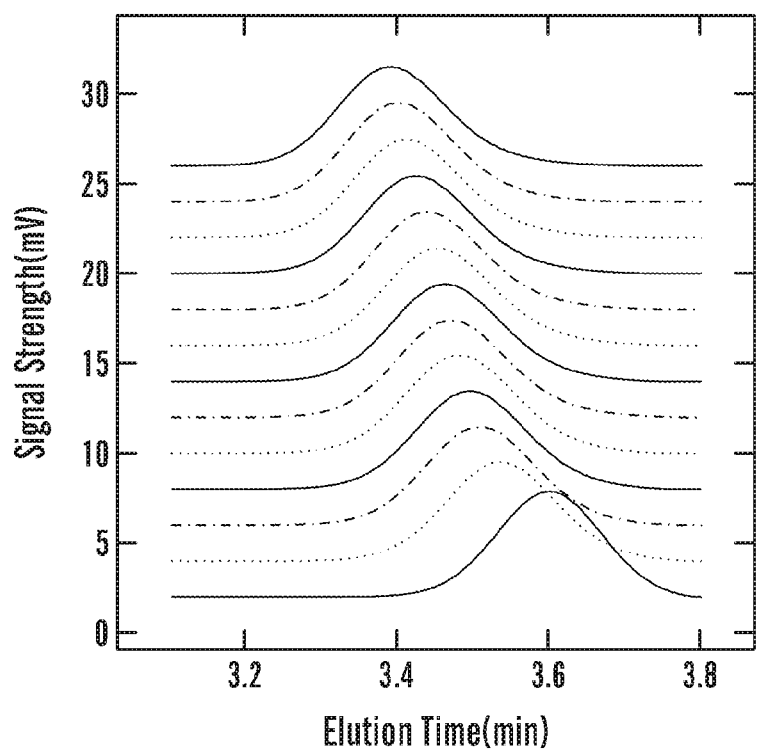
FIG. 18 shows GPC traces of styrene polymerization with trithioate OXCART at 100° C.
Figure 19:
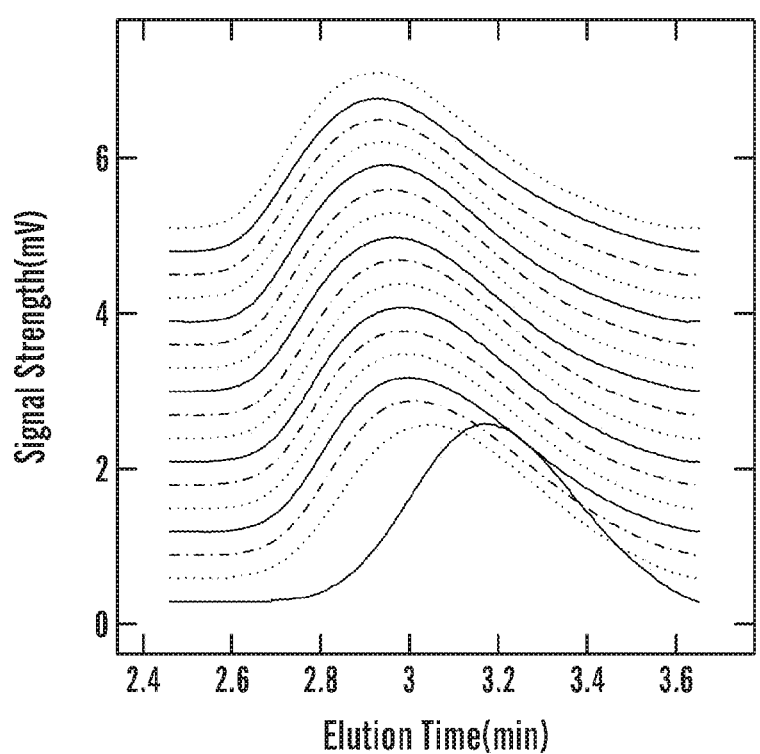
FIG. 19 shows GPC traces of styrene polymerization with trithioate OXCART at 125° C.
Figure 20:
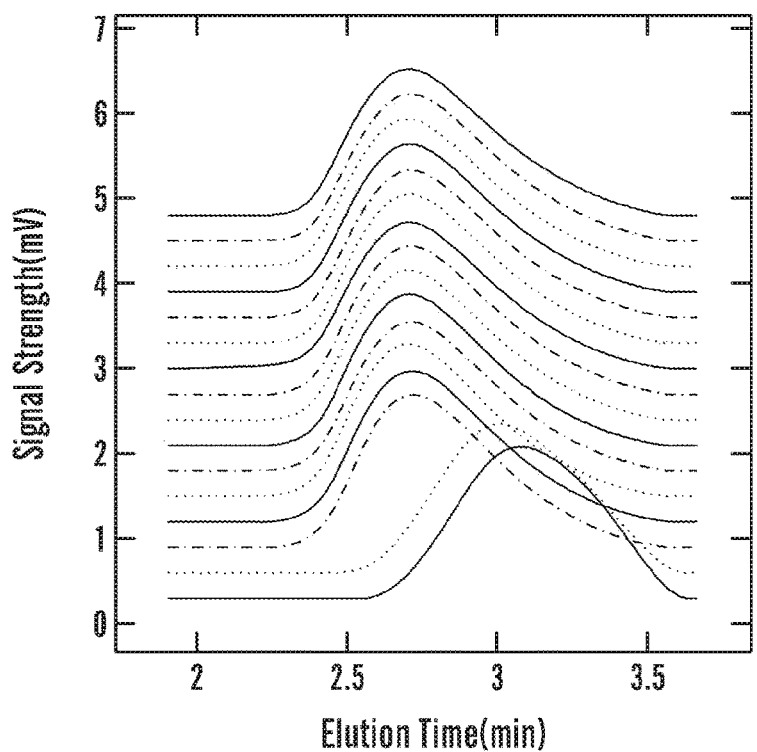
FIG. 20 shows GPC traces of styrene polymerization with trithioate OXCART at 135° C.

The GPC results of polymerization of styrene using trithioate OXCART at 100° C., 125° C., and 135° C. are shown in FIGS. 18-20, respectively.

Figure 21:
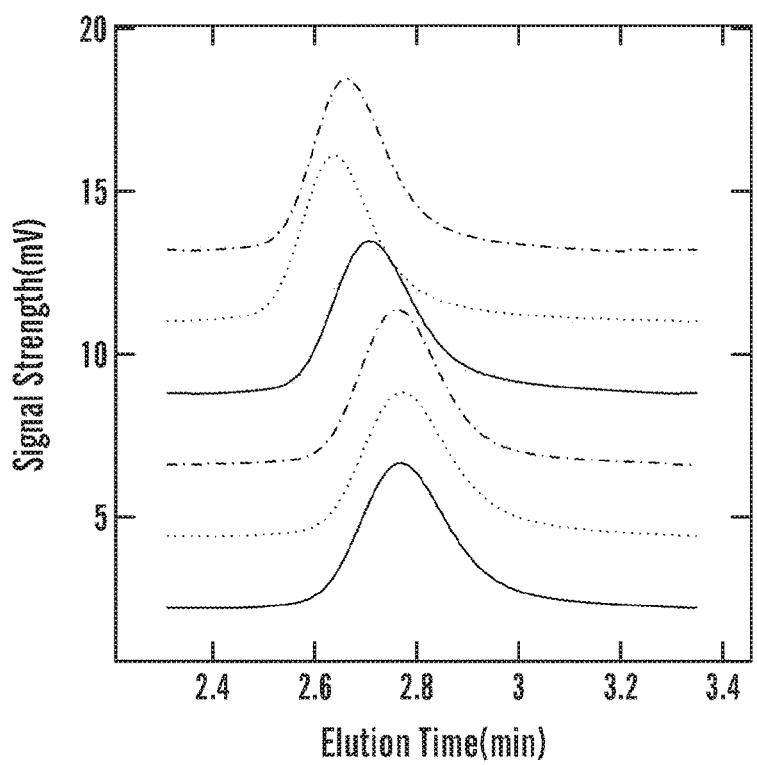
FIG. 21 shows GPC traces of styrene polymerization with trithioate OXCART at 100° C. with AIBN, 100° C. with benzoyl peroxide, 110° C. with AIBN, 110° C. with benzoyl peroxide, 120° C. with AIBN and 120° C. with benzoyl peroxide.

GPC traces of styrene polymerization with trithioate OXCART at 100° C. with AIBN, 100° C. with benzoyl peroxide, 110° C. with AIBN, 110° C. with benzoyl peroxide, 120° C. with AIBN and 120° C. with benzoyl peroxide are shown in FIG. 21.

Example 5—Conclusions and Discussion

Both the dithioate and trithioate versions of a CTA based on the R-group of 3-chloro-2-butanone work as CTA's. In addition, it was found that polymerization of both acrylates and styrenics with OXCART provided relatively high conversions and low PDI's. This is important, because one of the largest barriers to market of RAFT based polymers is that they do not work efficiently for styrenic blocks. As demonstrated in the present application, conversions in the 88%+ range can be achieved with the present invention. In addition, the synthesis of the molecules was straightforward with high yields (90%+) and high conversions (95%+), and would have low capital, material, and energy costs. This gives these molecules the potential to be one of the first industrially viable methods of producing RAFT based block copolymers, especially for styrenic BCP's (WO 2012/000022 to Moad et al., which is hereby incorporated by reference in its entirety).

With the low cost of materials and high conversion of styrene, these CTAs have high potential to be a process that could be commercialized to make styrenic-acrylate block copolymers. This would allow for a number of important developments. For some applications, if the conversion is driven to 90%+, a sequential BCP without any purification between polymerizations could be done. This would allow for the occasional styrene molecule in the following block; however, if it isn't critical that no styrene be in the following block, then this will save a purification and dissolution step. This would also likely reduce the amount of termination and thereby reduce the PDI of the following block. In addition, higher conversion would reduce the capital cost and separation cost of making the preliminary polystyrene block. A higher conversion of styrene to polystyrene will increase the amount of material made per volume of reaction solution, reducing the required size of the reaction vessel. Next, with less residual styrene, if a clean-up step between blocks is required, it leaves less monomer to recover and this should reduce the cost of recovery and reduce the amount of loss.

Finally, these CTAs have a residual ketone group. Ketones are functional groups that can be very easily modified. The CTAs can later be used to graft to or to add some functional group that allows for incorporation with some other desired material. For example, if an acrylate or methacrylate such as polyhydroxyethylmethacrylate or pHEMA is desired to be combined with a condensation polymer, such as PLGA, the CTA can be reduced down to an alcohol and then a condensation of the pHEMA polymer with the PLGA polymer will yield a pHEMA-PLGA BCP.

Example 6—Synthesis of 4-Oxo-4-(2-((((3-oxobutan-2-yl)thio)carbonothioyl)thio)-ethoxy)butanoic Acid ("Succinic OXCART")

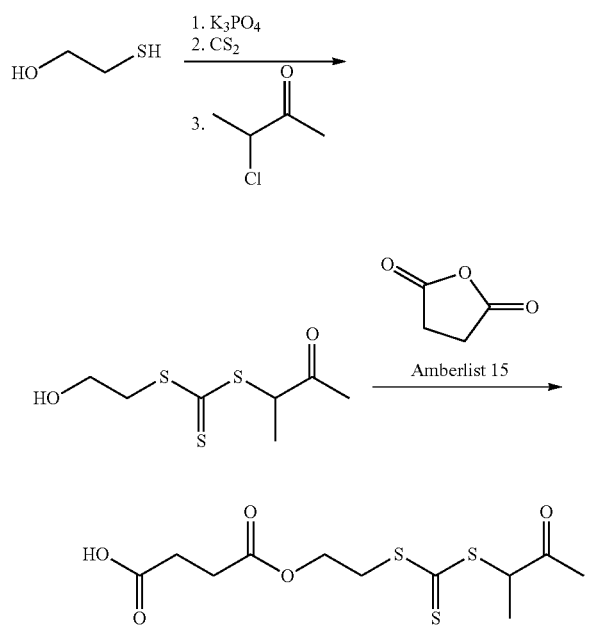

Figure 23:
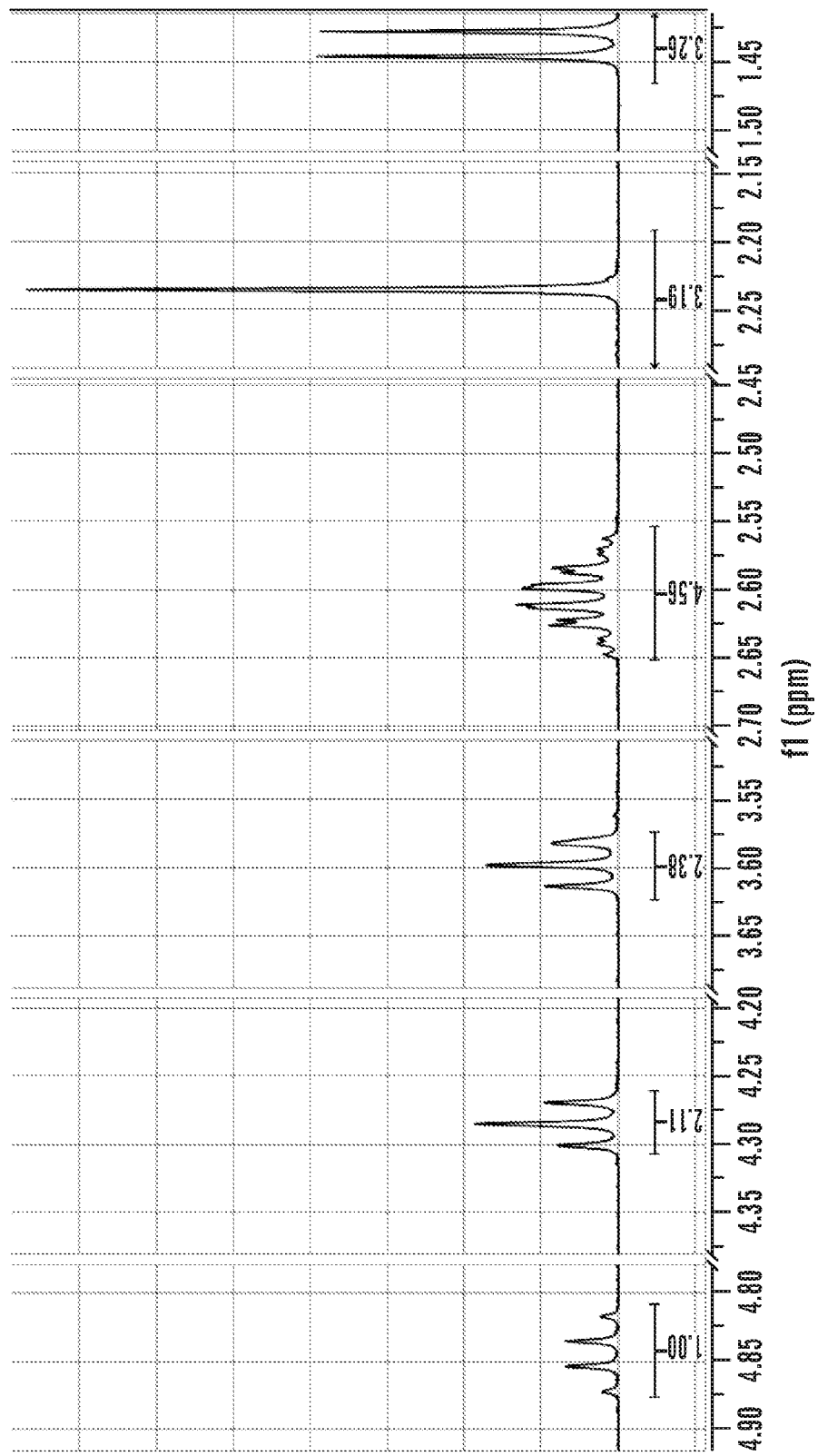
FIG. 23 shows proton NMR of 4-oxo-4-(2-((((3-oxobutan-2-yl)thio)carbonothioyl)thio)-ethoxy)butanoic acid.

Potassium phosphate tribasic (1.1 eq) and enough acetone to give about a 10-20% mass solution were added to a round bottom flask. The flask was submerged into a room temperature water bath and 2-mercaptoethanol (1 eq) was added to the flask. Next, carbon disulfide ($CS_2$) (1.5 eq) was slowly added over the course of 45 minutes. The reaction mixture was allowed to stir for 30 minutes before 3-chloro-2-butanone (2 eq) was added in. Upon completion of the reaction the solution was filtered and then the solvent was removed under vacuum to yield the intermediate: 2-hydroxyethyl (3-oxobutan-2-yl) carbonotrithioate. Following this, the intermediate was dissolved in dry THF, and succinic anhydride (1 eq) and N,N-dimethylbenzylamine (1 eq) were added. The solution was allowed to stir in a room temperature water bath for 2 hours. Upon completion of the reaction, the solvent was removed under vacuum and an aqueous workup in diethyl ether was completed. Following the aqueous workup, the solvent was once again removed under vacuum to supply the product confirmed by NMR (FIG. 23). (triplet 7.66-7.72, triplet 6.32-6.38 quartet 4.80-4.88, singlet 2.36-2.38, doublet 1.56-1.59) Example 7—Synthesis of 3-Oxobutan-2-yl 1H-pyrrole-1-carbodithioate ("Pyrrole OXCART")

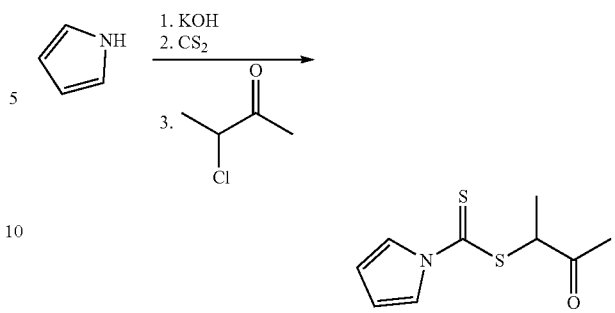

Figure 24:
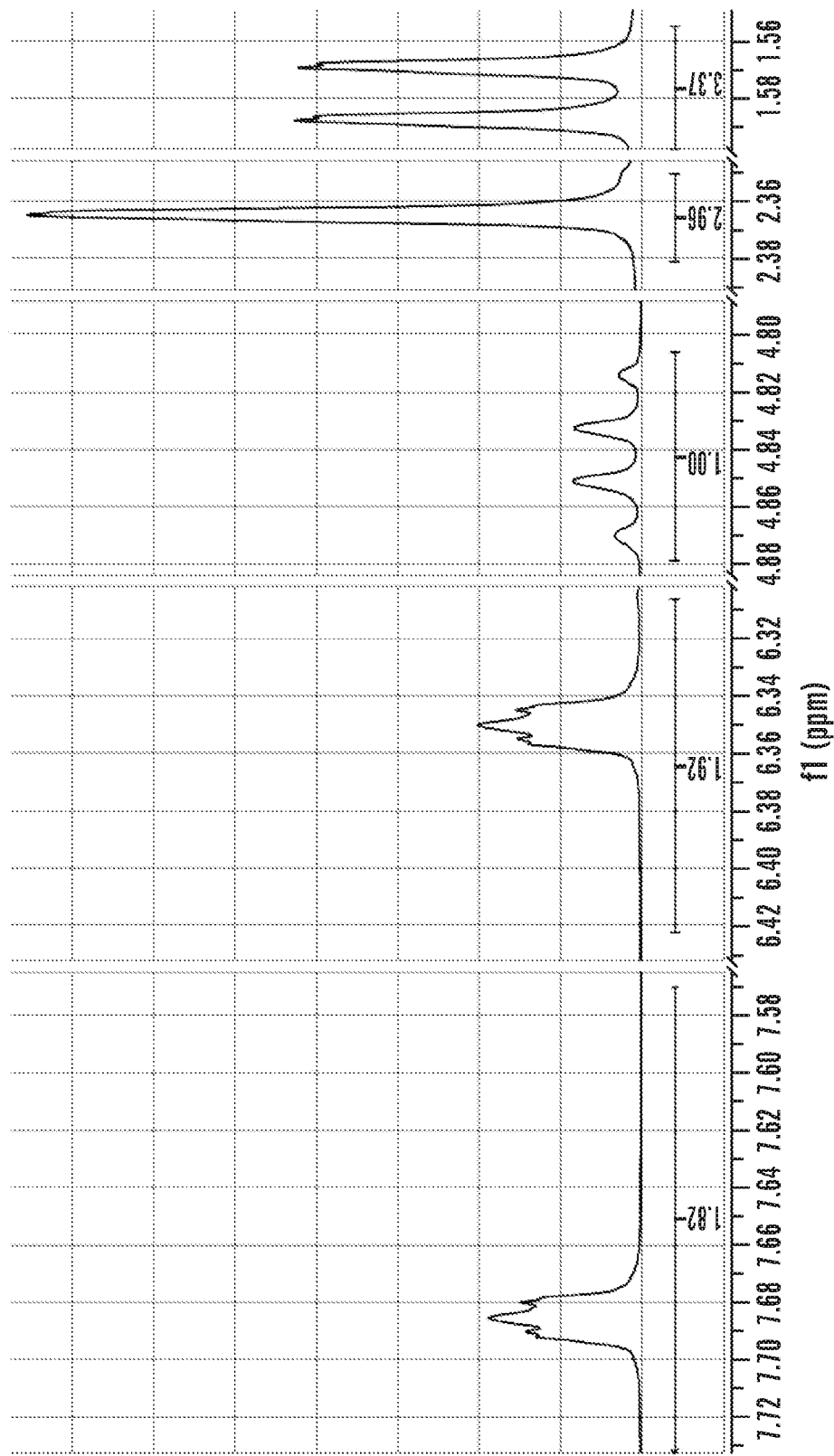
FIG. 24 shows proton NMR of 3-oxobutan-2-yl 1H-pyrrole-1-carbodithioate.

Pyrrole (1 eq) was dissolved in DMF to provide a 20% mass solution. Potassium hydroxide (1.1 eq) was added to deprotonate the pyrrole. After allowing to stir for 4 hours, carbon disulfide (1.5 eq) was added and allowed to stir for 4 hours. Finally, 3-chloro-2-butanone (2 eq) was added and allowed to stir for 4 hours. Upon completion of the reaction, the DMF was removed under reduced pressure and an aqueous workup is done to collect the product. Finally, the extracting solvent was removed under reduced pressure to yield the desired product confirmed by NMR (FIG. 24). $^1$H NMR ($CDCl_3$): (quartet 4.8-4.9, triplet 4.25-435, triplet 3.55-3.65, multiplet 2.55-2.65, singlet, 2.20-2.30, doublet 1.35-1.45).

Example 8—Polymerization of Butyl Acrylate with Pyrrole OXCART

Butyl acrylate was polymerized via RAFT using the Pyrrole OXCART CTA. For every gram of monomer added 0.00426 g of CTA was added to give a target molecular weight of 50 kDa. The solution was then diluted down to 50% solids and 0.3:1 molar ratio (0.77:1 mass ratio) of AIBN:CTA was added. Finally, the reaction was purged for 15 minutes and reacted at 70° C.

Example 9—Polymerization of Styrene with Pyrrole OXCART

Styrene was polymerized via RAFT using the Pyrrole OXCART CTA. For every gram of monomer added 0.00426 g of CTA was added to give a target molecular weight of 50 kDa. The solution was then diluted down to 50% solids and 0.3:1 molar ratio (0.231:1 mass ratio) of AIBN:CTA was added. Finally, the reaction was purged for 15 minutes and reacted at 100° C.

Example 10—Polymerization of Butyl Acrylate with Succinic OXCART

Butyl acrylate was polymerized via RAFT using the Succinic OXCART CTA. For every gram of monomer added 0.0062 g of CTA was added to give a target molecular weight of 50 kDa. The solution was then diluted down to 50% solids and 0.3:1 molar ratio (0.175:1 mass ratio) of AIBN:CTA was added. Finally, the reaction is purged for 15 minutes and reacted at 100° C.

Example 11—Results of Examples 6-10

Figure 25:
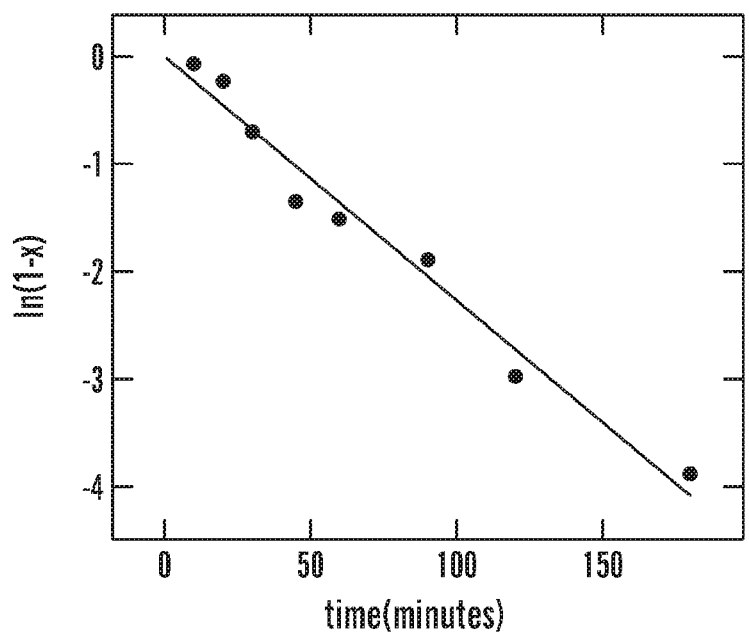
FIG. 25 is a plot showing the linearity of ln 1–x versus time, indicating a first order reaction rate for butyl acrylate.
Figure 26:
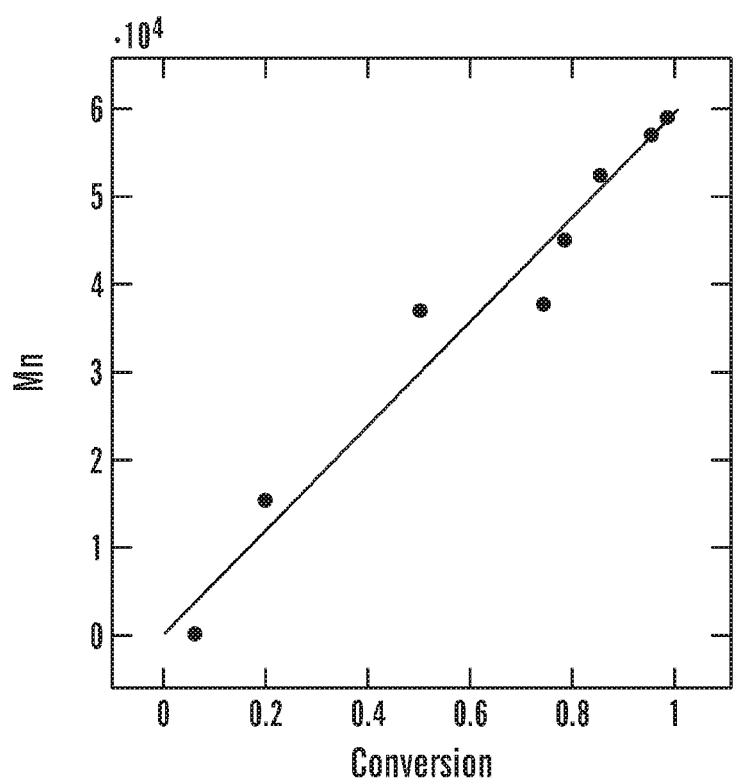
FIG. 26 is a plot of molecular weight versus conversion showing that the CTA functions as a CTA and controls the molecular weight growth of the butyl acrylate polymer.
Figure 27:
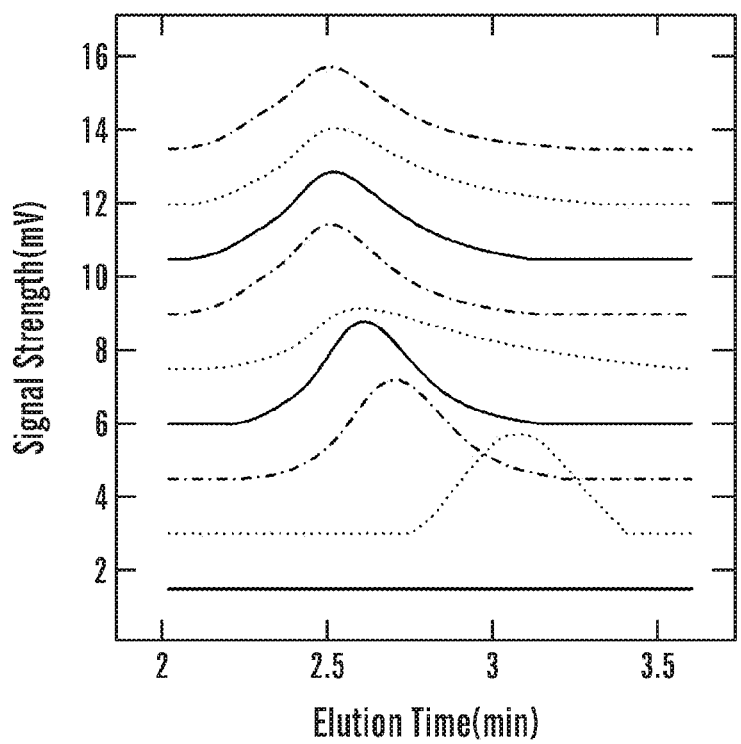
FIG. 27 shows GPC traces for the polymerization of butyl acrylate over time. Time increases with increment upward along y.

Polymerization of Butyl Acrylate with Pyrrole OXCART
Butyl acrylate polymerized with Pyrrole OXCART showed linear ln(1−x) versus time indicating first order reaction kinetics and good initiator system (FIG. 25). It also showed a linear molecular weight versus conversion plot indicating that the polymerization was controlled (FIG. 26). The GPC's showed a continual increase in molecular weight over time without a substantial increase in peak broadening also indicating good control over molecular weight (FIG. 27). Finally, the PDI of each aliquot was low further indicating good control over polymerization (Table 5).

TABLE 5

Results of Polymerization of Butyl Acrylate Over Time
Butyl Acrylate Polymerization using Pyrrole OXCART

| Time | Conversion | Mn | PDI |
|---|---|---|---|
| 10 | 6% | 0.2 kDa | 1.47 |
| 20 | 20% | 15 kDa | 1.13 |
| 30 | 50% | 37 kDa | 1.13 |
| 45 | 74% | 38 kDa | 1.34 |
| 60 | 78% | 45 kDa | 1.12 |
| 90 | 85% | 52 kDa | 1.27 |
| 120 | 95% | 57 kDa | 1.22 |
| 180 | 98% | 59 kDa | 1.27 |

Polymerization of Styrene with Pyrrole OXCART

Figure 28:
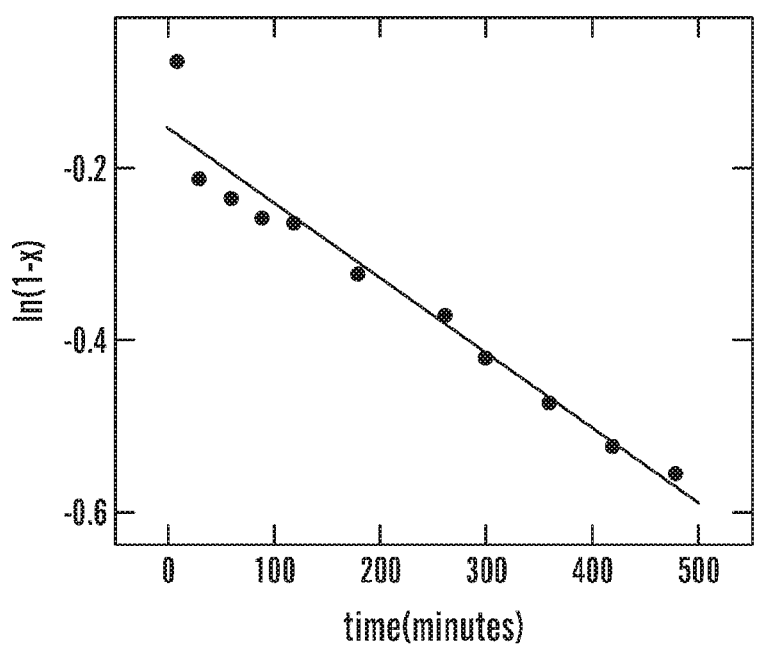
FIG. 28 is a plot showing the linearity of ln 1–x versus time, indicating a first order reaction rate for styrene.
Figure 29:
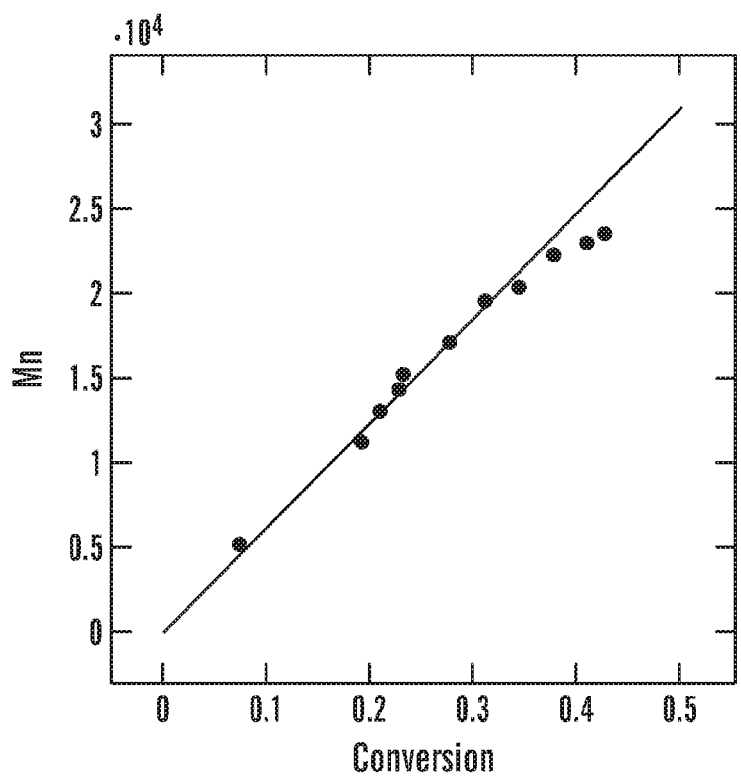
FIG. 29 is a plot of molecular weight versus conversion showing that the CTA functions as a CTA and controls the molecular weight growth of the styrene polymer.
Figure 30:
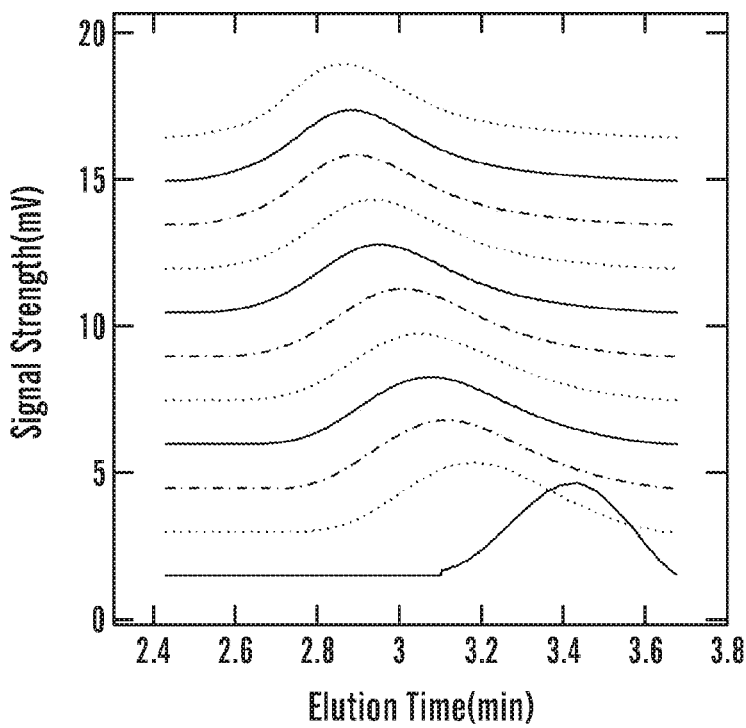
FIG. 30 shows GPC traces for the polymerization of styrene over time. Time increases with increment upward along y.

Butyl acrylate polymerized with Pyrrole OXCART showed linear ln(1−x) versus time indicating first order reaction kinetics and good initiator system (FIG. 28). It also showed a linear molecular weight versus conversion plot, indicating that the polymerization was controlled (FIG. 29). The GPC's showed a continual increase in molecular weight over time without a substantial increase in peak broadening also indicating good control over molecular weight (FIG. 30). Finally, the PDI of each aliquot was low further indicating good control over polymerization (Table 6).

TABLE 6

Results of Polymerization of Styrene Over Time
Styrene Polymerization using Pyrrole OXCART

| Time | Conversion | Mn | PDI |
|---|---|---|---|
| 10 | 7% | 5 kDa | 1.27 |
| 30 | 19% | 11 kDa | 1.23 |
| 60 | 21% | 13 kDa | 1.23 |
| 90 | 23% | 14 kDa | 1.22 |
| 120 | 23% | 15 kDa | 1.22 |
| 180 | 28% | 17 kDa | 1.20 |
| 260 | 31% | 19 kDa | 1.18 |
| 300 | 34% | 20 kDa | 1.17 |
| 360 | 38% | 22 kDa | 1.17 |
| 420 | 41% | 23 kDa | 1.17 |
| 480 | 43% | 24 kDa | 1.16 |

Polymerization of Butyl Acrylate with Succinic OXCART

Figure 31:
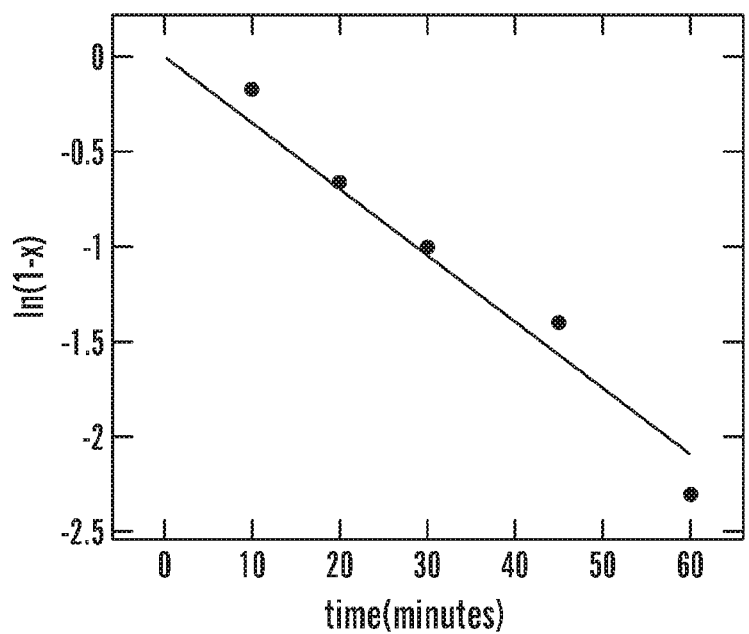
FIG. 31 is a plot showing the linearity of ln 1–x versus time, indicating a first order reaction rate for butyl acrylate.
Figure 32:
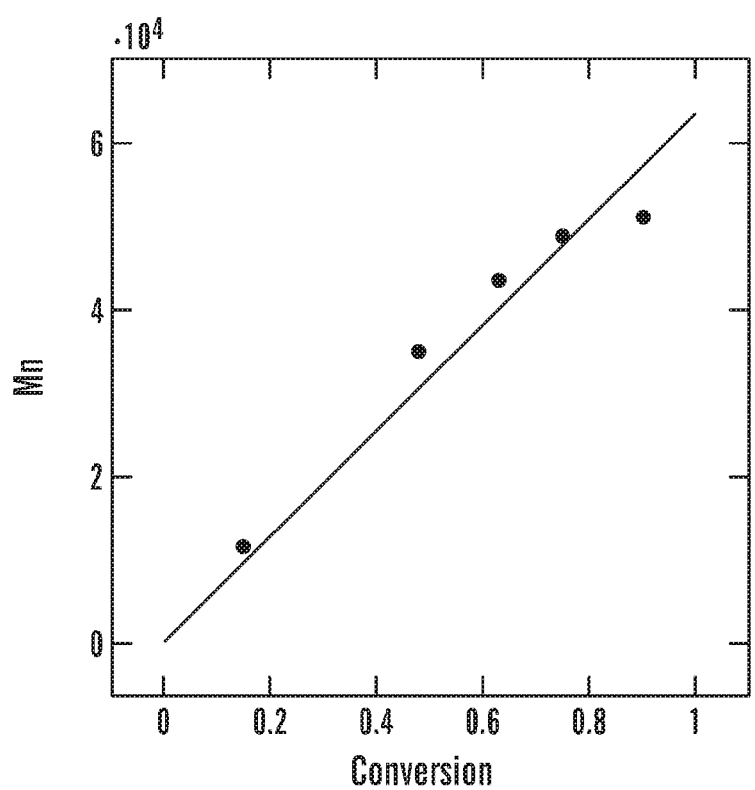
FIG. 32 is a plot of molecular weight versus conversion showing that the CTA functions as a CTA and controls the molecular weight growth of the butyl acrylate polymer.
Figure 33:
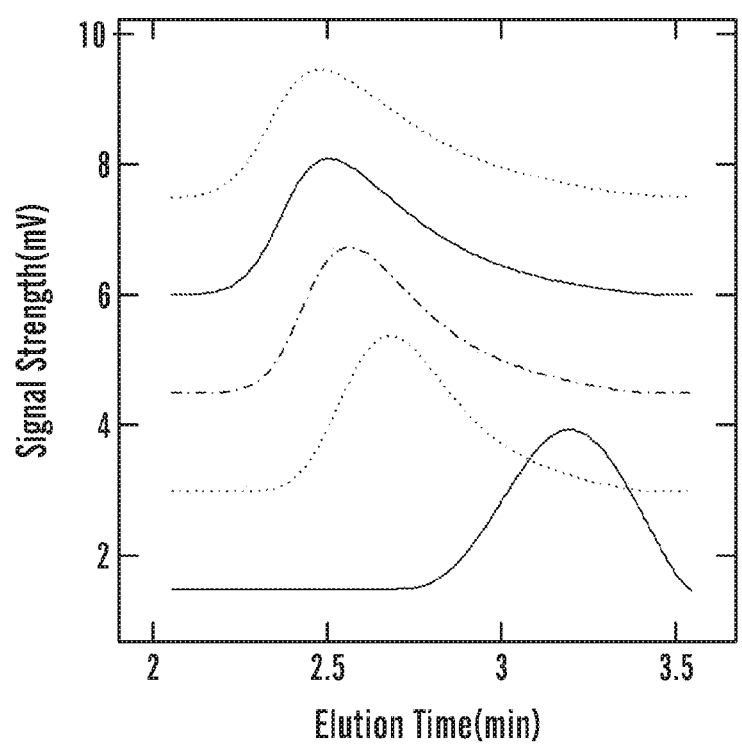
FIG. 33 shows GPC traces for the polymerization of butyl acrylate over time. Time increases with increment upward along y.

Butyl acrylate polymerized with Pyrrole OXCART showed linear ln(1-x) versus time indicating first order reaction kinetics and good initiator system (FIG. 31). It also showed a linear molecular weight versus conversion plot, indicating that the polymerization was controlled (FIG. 32). The GPC's showed a continual increase in molecular weight over time without a substantial increase in peak broadening also indicating good control over molecular weight (FIG. 33). Finally, the PDI of each aliquot was low further indicating good control over polymerization (Table 7).

TABLE 7

Results of Polymerization of Butyl Acrylate Over Time
Butyl Acrylate Polymerization using Succinic OXCART

| Time | Conversion | Mn | PDI |
|---|---|---|---|
| 10 | 15% | 12 kDa | 1.22 |
| 20 | 48% | 35 kDa | 1.14 |
| 30 | 63% | 43 kDa | 1.18 |
| 45 | 75% | 48 kDa | 1.22 |
| 60 | 90% | 51 kDa | 1.25 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound having the structure of formula (I):

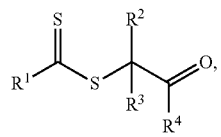

wherein $R^1$ is aryl or $SC_{1-20}$ alkyl, wherein the aryl and $SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$, $R^2$ is $C_{1-6}$ alkyl, $R^3$ is H or $C_{1-6}$ alkyl, $R^4$ is H or $C_{1-6}$ alkyl, $R^5$ is H or $C_{1-6}$ alkyl, $R^6$ is H or $C_{1-6}$ alkyl, and $R^7$ is H or $C_{1-6}$ alkyl, with the proviso that when $R^4$ is methyl then $R^1$ is not aryl or —S-t-Bu.

2. The compound of claim 1 having the structure selected from the group consisting of:

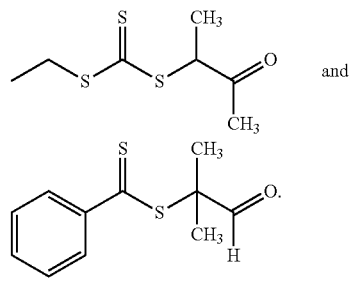

3. A process for the preparation of a compound of formula (I):

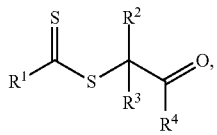

wherein
R$^1$ is aryl or —SC$_{1-20}$ alkyl, wherein the aryl and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H or C$_{1-6}$ alkyl,
R$^6$ is H or C$_{1-6}$ alkyl, and
R$^7$ is H or C$_{1-6}$ alkyl,
with the proviso that when R$^4$ is methyl then R$^1$ is not aryl or —S-t-Bu, said process comprising:
providing a first intermediate compound of formula (II):

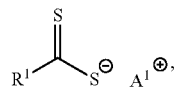

wherein A$^{1\oplus}$ is a suitable cation; and
forming the compound of formula (I) from the first intermediate compound of formula (II).

4. The process according to claim 3, wherein A$^{1\oplus}$ is selected from the group consisting of K$^+$, Na$^+$, Li$^+$, triethyl ammonium cation, and piperidinium cation.

5. The process according to claim 3, wherein said forming the compound of formula (I) comprises:
reacting the first intermediate compound of formula (II) with a compound of formula (III):

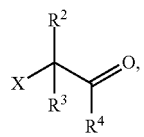

wherein X is a leaving group,
under conditions effective to produce the compound of formula (I).

6. The process according to claim 5, wherein X is a halogen.

7. The process according to claim 6, wherein X is Cl.

8. The process according to claim 3 further comprising:
providing a second intermediate compound of formula (IV)

$$R^{1\ominus}A^{2\oplus} \quad (IV),$$

wherein A$^{2\oplus}$ is a suitable cation; and
forming the first intermediate compound of formula (II) from the second intermediate compound of formula (IV).

9. The process according to claim 8, wherein A$^{2\oplus}$ is selected from the group consisting of K$^+$, Na$^+$, Li$^+$, triethyl ammonium cation, and piperidinium cation.

10. The process according to claim 8, wherein said forming the first intermediate compound of formula (II) comprises:
reacting the second intermediate compound of formula (IV) with carbon disulfide under conditions effective to produce the first intermediate compound of formula (II).

11. The process according to claim 8 further comprising:
providing a compound of formula (V):

$$R^1H \quad (V), \text{ and}$$

reacting the compound of formula (V) with a base to form the second intermediate compound of formula (IV).

12. The process according to claim 11, wherein the base is selected from the group consisting of K$_3$PO$_4$*xH$_2$O, Na$_3$PO$_4$*xH$_2$O, Li$_3$PO$_4$, NaH, Et$_3$N, piperidine, morpholine, alkali hydroxides; and wherein x is 0 to 10.

13. The process according to claim 12, wherein the base is K$_3$PO$_4$*3H$_2$O.

14. A process for the synthesis of a polymer comprising:
providing a monomer composition;
providing a chain transfer agent of formula (I):

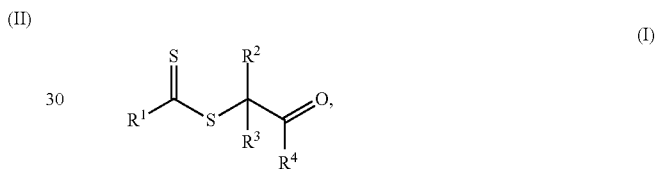

wherein
R$^1$ is aryl or —SC$_{1-20}$ alkyl, wherein aryl and —SC$_{1-20}$ alkyl can be optionally substituted with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl,
R$^3$ is H or C$_{1-6}$ alkyl,
R$^4$ is H or C$_{1-6}$ alkyl,
R$^5$ is H or C$_{1-6}$ alkyl,
R$^6$ is H or C$_{1-6}$ alkyl, and
R$^7$ is H or C$_{1-6}$ alkyl; and
polymerizing the monomer composition through controlled free radical polymerization with the chain transfer agent to form the polymer.

15. The process of claim 14, wherein the chain transfer agent has formula (I):

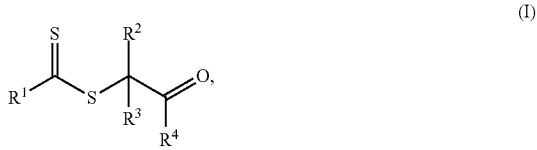

wherein
R$^1$ is aryl or —SC$_{1-20}$ alkyl, wherein aryl and —SC$_{1-20}$ alkyl can be optionally selected with 1-5 substituents independently selected in each occurrence thereof from the group consisting of H, C$_{1-6}$ alkyl, halogen, —OR$^5$, —SR$^5$, and —NR$^6$R$^7$,
R$^2$ is C$_{1-6}$ alkyl, $R^3$ is H or $C_{1-6}$ alkyl,
$R^4$ is H or $C_{1-6}$ alkyl,
$R^5$ is H or $C_{1-6}$ alkyl,
$R^6$ is H or $C_{1-6}$ alkyl, and
$R^7$ is H or $C_{1-6}$ alkyl,
with the proviso that when $R^4$ is methyl then $R^1$ is not aryl or —S-t-Bu.

16. The process of claim 14, wherein the chain transfer agent has the structure selected from the group consisting of:

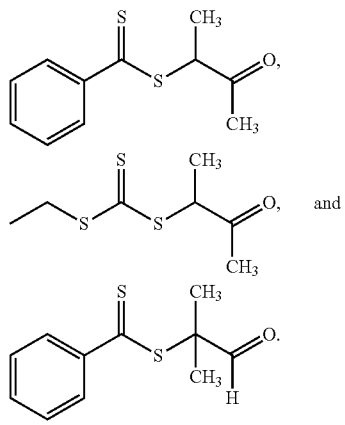

17. The process of claim 14, wherein said monomer composition comprises one or more monomers.

18. The process of claim 17, wherein the one or more monomers is selected from the group consisting of vinyl aromatics, acrylate, and methacrylate.

19. The process of claim 17, wherein the one or more monomers is selected from the group consisting of styrene, butyl acrylate, methyl acrylate, and methyl methacrylate.

20. The process of claim 14, wherein said polymerizing is carried out by reversible addition-fragmentation chain-transfer polymerization (RAFT), in the presence of a free radical initiator and a solvent.

21. The process of claim 20, wherein said polymerizing is carried out at a temperature of 0 to 200° C.

22. The process of claim 20, wherein said solvent is selected from the group consisting of toluene, THF, chloroform, cyclohexane, dioxane, dimethyl sulfoxide, dimethyl formamide, acetone, acetonitrile, n-butanol, n-pentanol, chlorobenzene, dichloromethane, diethylether, tert-butanol, 1,2,-dichloroethylene, diisopropylether, ethanol, ethylacetate, ethylmethylketone, heptane, hexane, isopropylalcohol, isoamylalcohol, methanol, pentane, n-propylalcohol, pentachloroethane, 1,1,2,2,-tetrachloroethane, 1,1,1,-trichloroethane, tetrachloroethylene, tetrachloromethane, trichloroethylene, water, xylene, benzene, nitromethane, glycerol, and a mixture thereof.

23. The process of claim 20, wherein said solvent further includes stabilizers, surfactants, or dispersants.

24. The process of claim 20, wherein the free radical initiator is selected from the group consisting of benzoyl peroxide and azobisisobutyronitrile.

25. The process of claim 14, wherein said polymerizing is carried out in a solvent with the monomer having a concentration, when dissolved in the solvent, ranging from 1% to 90 wt %.

26. The process of claim 14, wherein polymer is a homopolymer, copolymer, block copolymer, or statistical copolymer.

27. The process of claim 14, wherein polymer is a multi block copolymer.

28. The process of claim 14, wherein the polymer has a polydispersity index (DPI) of less than 2.

29. The process of claim 14, wherein the polymer has a polydispersity index (DPI) of less than 1.5.

30. The process of claim 14, wherein the polymer has a polydispersity index (DPI) of less than 1.2.

31. The process of claim 14, wherein the chain transfer agent having the structure of formula (I) is supported on an inert carrier.

32. The process of claim 14, wherein said polymerizing is carried out to produce a homopolymer, copolymer, or block copolymer having a linear or branched-chain structure.

33. The process of claim 32, wherein said polymerizing is carried out under conditions effective to produce the homopolymer, copolymer, or block copolymer with a molecular weight of at least 1 KDa without gelation.

34. The process of claim 32 further comprising:
chemically modifying the homopolymer, copolymer, or block copolymer with a crosslinking agent, allowing the homopolymer, copolymer, or block copolymer to undergo a crosslinking reaction at an elevated temperature.

35. The process of claim 32 further comprising:
chemically modifying the homopolymer, copolymer, or block copolymer with a reagent to confer an acidic or basic functionality to the homopolymer, copolymer, or block copolymer,
making the homopolymer, copolymer, or block copolymer a pH adjusting agent.

36. The process of claim 32 further comprising:
chemically modifying the homopolymer, copolymer, or block copolymer with a reagent to confer a biocidic functionality to the homopolymer, copolymer, or block copolymer, making the homopolymer, copolymer, or block copolymer a biocide agent.

37. The process of claim 32, wherein the homopolymer is polystyrene.

38. The process of claim 14, wherein said polymerizing is carried out to form the thermoplastic block copolymer.

39. The process of claim 38 further comprising:
providing a radically polymerizable monomer; and
polymerizing the radically polymerizable monomer through reversible addition-fragmentation chain-transfer polymerization (RAFT) with the thermoplastic block copolymer as a macromolecular chain transfer agent to add an additional block to the block copolymer.

40. A compound having the structure of formula (I):

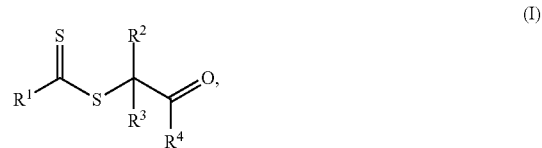

wherein
$R^1$ is aryl or —$SC_{1-20}$ alkyl, wherein the aryl and —$SC_{1-20}$ alkyl can be optionally substituted with 1-5 substituents independently selected in each occurrence thereof from the group consisting of H, $C_{1-6}$ alkyl, halogen, —$OR^5$, —$SR^5$, and —$NR^6R^7$,
$R^2$ is $C_{1-6}$ alkyl, $R^3$ is H or $C_{1-6}$ alkyl,
$R^4$ is H or $C_{1-6}$ alkyl,
$R^5$ is H, $C_{1-6}$ alkyl, or —C(O)—(CH$_2$)$_n$—COOH,
$R^6$ is H or $C_{1-6}$ alkyl,
$R^7$ is H or $C_{1-6}$ alkyl, and
n is 1, 2, 3, 4, 5, or 6,
with the proviso that when $R^4$ is methyl then $R^1$ is not aryl or —S-t-Bu.

41. The compound of claim 40 having the structure selected from the group consisting of:

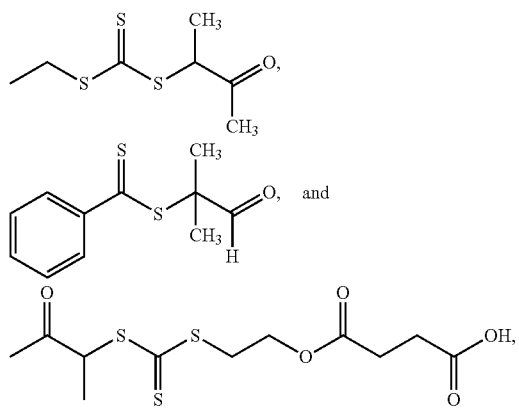

42. A process for the preparation of a compound of formula (I):

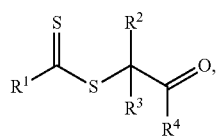

wherein
$R^1$ is aryl or —SC$_{1-20}$ alkyl, wherein the aryl and —SC$_{1-20}$ alkyl can be optionally substituted with 1-5 substituents independently selected in each occurrence thereof from the group consisting of H, $C_{1-6}$ alkyl, halogen, —OR$^5$, —SR$^5$, and —NR$^6$R$^7$,
$R^2$ is $C_{1-6}$ alkyl,
$R^3$ is H or $C_{1-6}$ alkyl,
$R^4$ is H or $C_{1-6}$ alkyl,
$R^5$ is H, $C_{1-6}$ alkyl, or —C(O)—(CH$_2$)$_n$—COOH,
$R^6$ is H or $C_{1-6}$ alkyl,
$R^7$ is H or $C_{1-6}$ alkyl, and
n is 1, 2, 3, 4, 5, or 6,
with the proviso that when $R^4$ is methyl then $R^1$ is not aryl or —S-t-Bu, said process comprising:
providing a first intermediate compound of formula (II):

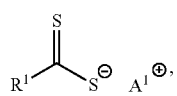

wherein $A^{1\oplus}$ is a suitable cation; and
forming the compound of formula (I) from the first intermediate compound of formula (II).

43. The process according to claim 42, wherein $A^{1\oplus}$ is selected from the group consisting of K$^+$, Na$^+$, Li$^+$, triethyl ammonium cation, and piperidinium cation.

44. The process according to claim 42, wherein said forming the compound of formula (I) comprises:
reacting the first intermediate compound of formula (II) with a compound of formula (III):

wherein X is a leaving group,
under conditions effective to produce the compound of formula (I).

45. The process according to claim 44, wherein X is a halogen.

46. The process according to claim 45, wherein X is Cl.

47. The process according to claim 42 further comprising:
providing a second intermediate compound of formula (IV)

wherein $A^{2\oplus}$ is a suitable cation; and
forming the first intermediate compound of formula (II) from the second intermediate compound of formula (IV).

48. The process according to claim 47, wherein $A^{2\oplus}$ is selected from the group consisting of K$^+$, Na$^+$, Li$^+$, triethyl ammonium cation, and piperidinium cation.

49. The process according to claim 47, wherein said forming the first intermediate compound of formula (II) comprises:
reacting the second intermediate compound of formula (IV) with carbon disulfide under conditions effective to produce the first intermediate compound of formula (II).

50. The process according to claim 47 further comprising:
providing a compound of formula (V):

reacting the compound of formula (V) with a base to form the second intermediate compound of formula (IV).

51. The process according to claim 50, wherein the base is selected from the group consisting of K$_3$PO$_4$*xH$_2$O, Na$_3$PO$_4$*xH$_2$O, Li$_3$PO$_4$, NaH, Et$_3$N, piperidine, morpholine, alkali hydroxides; and wherein x is 0 to 10.

52. The process according to claim 51, wherein the base is K$_3$PO$_4$*3H$_2$O.

53. A process for the synthesis of a polymer comprising:
providing a monomer composition;
providing a chain transfer agent of formula (I):

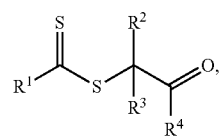

wherein
R¹ is aryl or —SC₁₋₂₀ alkyl, wherein the aryl and —SC₁₋₂₀ alkyl can be optionally substituted with 1-5 substituents independently selected in each occurrence thereof from the group consisting of H, C₁₋₆ alkyl, halogen, —OR⁵, —SR⁵, and —NR⁶R⁷,
R² is C₁₋₆ alkyl,
R³ is H or C₁₋₆ alkyl,
R⁴ is H or C₁₋₆ alkyl,
R⁵ is H, C₁₋₆ alkyl, or —C(O)—(CH₂)ₙ—COOH,
R⁶ is H or C₁₋₆ alkyl,
R⁷ is H or C₁₋₆ alkyl, and
n is 1, 2, 3, 4, 5, or 6; and
polymerizing the monomer composition through controlled free radical polymerization with the chain transfer agent to form the polymer.

54. The process of claim 53, wherein the chain transfer agent has formula (I):

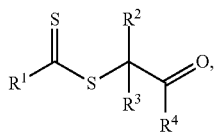
(I)

wherein
R¹ is aryl or —SC₁₋₂₀ alkyl, wherein the aryl and —SC₁₋₂₀ alkyl can be optionally substituted with 1-5 substituents independently selected in each occurrence thereof from the group consisting of H, C₁₋₆ alkyl, halogen, —OR⁵, —SR⁵, and —NR⁶R⁷,
R² is C₁₋₆ alkyl,
R³ is H or C₁₋₆ alkyl,
R⁴ is H or C₁₋₆ alkyl,
R⁵ is H, C₁₋₆ alkyl, or —C(O)—(CH₂)ₙ—COOH,
R⁶ is H or C₁₋₆ alkyl,
R⁷ is H or C₁₋₆ alkyl, and
n is 1, 2, 3, 4, 5, or 6,
with the proviso that when R⁴ is methyl then R¹ is not aryl or —S-t-Bu.

55. The process of claim 53, wherein the chain transfer agent has the structure selected from the group consisting of:

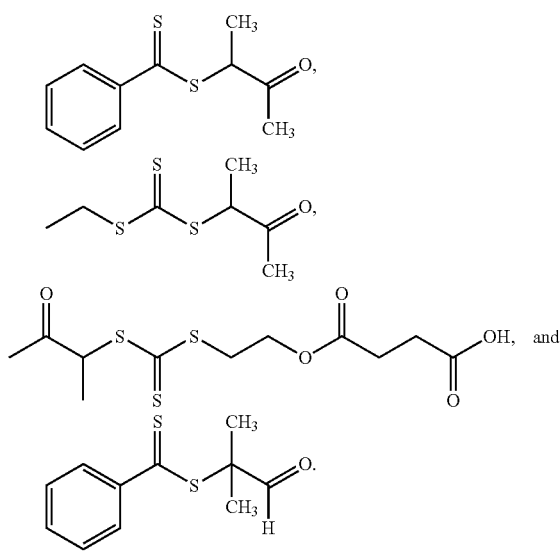

56. The process of claim 53, wherein said monomer composition comprises one or more monomers.

57. The process of claim 56, wherein the one or more monomers is selected from the group consisting of vinyl aromatics and acrylates.

58. The process of claim 56, wherein the one or more monomers is selected from the group consisting of styrene, butyl acrylate, methyl acrylate, and methyl methacrylate.

59. The process of claim 53, wherein said polymerizing is carried out by reversible addition-fragmentation chain-transfer polymerization (RAFT), in the presence of a free radical initiator and a solvent.

60. The process of claim 59, wherein said polymerizing is carried out at a temperature of 0 to 200° C.

61. The process of claim 59, wherein said solvent is selected from the group consisting of toluene, THF, chloroform, cyclohexane, dioxane, dimethyl sulfoxide, dimethyl formamide, acetone, acetonitrile, n-butanol, n-pentanol, chlorobenzene, dichloromethane, diethylether, tert-butanol, 1,2,-dichloroethylene, diisopropylether, ethanol, ethylacetate, ethylmethylketone, heptane, hexane, isopropylalcohol, isoamylalcohol, methanol, pentane, n-propylalcohol, pentachloroethane, 1,1,2,2,-tetrachloroethane, 1,1,1,-trichloroethane, tetrachloroethylene, tetrachloromethane, trichloroethylene, water, xylene, benzene, nitromethane, glycerol, and a mixture thereof.

62. The process of claim 59, wherein said solvent further includes stabilizers, surfactants, or dispersants.

63. The process of claim 59, wherein the free radical initiator is selected from the group consisting of benzoyl peroxide and azobisisobutyronitrile.

64. The process of claim 53, wherein said polymerizing is carried out in a solvent with the monomer having a concentration, when dissolved in the solvent, ranging from 1% to 90 wt %.

65. The process of claim 53, wherein polymer is a homopolymer, copolymer, block copolymer, or statistical copolymer.

66. The process of claim 53, wherein polymer is a multi block copolymer.

67. The process of claim 53, wherein the polymer has a polydispersity index (DPI) of less than 2.

68. The process of claim 53, wherein the polymer has a polydispersity index (DPI) of less than 1.5.

69. The process of claim 53, wherein the polymer has a polydispersity index (DPI) of less than 1.2.

70. The process of claim 53, wherein the chain transfer agent having the structure of formula (I) is supported on an inert carrier.

71. The process of claim 53, wherein said polymerizing is carried out to produce a homopolymer, copolymer, or block copolymer having a linear or branched-chain structure.

72. The process of claim 71, wherein said polymerizing is carried out under conditions effective to produce the homopolymer, copolymer, or block copolymer with a molecular weight of at least 1 KDa without gelation.

73. The process of claim 71 further comprising:
chemically modifying the homopolymer, copolymer, or block copolymer with a crosslinking agent, allowing the homopolymer, copolymer, or block copolymer to undergo a crosslinking reaction at an elevated temperature.

74. The process of claim 71 further comprising:
chemically modifying the homopolymer, copolymer, or block copolymer with a reagent to confer an acidic or basic functionality to the homopolymer, copolymer, or block copolymer, making the homopolymer, copolymer, or block copolymer a pH adjusting agent.

75. The process of claim 71 further comprising:
chemically modifying the homopolymer, copolymer, or block copolymer with a reagent to confer a biocidic functionality to the homopolymer, copolymer, or block copolymer, making the homopolymer, copolymer, or block copolymer a biocide agent.

76. The process of claim 71, wherein the homopolymer is polystyrene.

77. The process of claim 53, wherein said polymerizing is carried out to form the thermoplastic block copolymer.

78. The process of claim 77 further comprising:
providing a radically polymerizable monomer; and
polymerizing the radically polymerizable monomer through reversible addition-fragmentation chain-transfer polymerization (RAFT) with the thermoplastic block copolymer as a macromolecular chain transfer agent to add an additional block to the block copolymer.

* * * * *

UNITED STATES PATENT AND TRADEMARK OFFICE
CERTIFICATE OF CORRECTION

PATENT NO. : 10,968,173 B2  
APPLICATION NO. : 16/315432  
DATED : April 6, 2021  
INVENTOR(S) : Cochran et al.

Page 1 of 1

It is certified that error appears in the above-identified patent and that said Letters Patent is hereby corrected as shown below:

In the Claims

In Claim 1, at Column 28, Line 34, delete "$SC_{1-20}$ alkyl" and insert -- –$SC_{1-20}$ alkyl--.

In Claim 1, at Column 28, Lines 34–35, delete "$SC_{1-20}$ alkyl" and insert -- –$SC_{1-20}$ alkyl--.

In Claim 41, at Column 33, Line 25, delete "," and insert --.--.

Signed and Sealed this  
Sixth Day of July, 2021

Drew Hirshfeld  
*Performing the Functions and Duties of the*  
*Under Secretary of Commerce for Intellectual Property and*  
*Director of the United States Patent and Trademark Office*